(12) United States Patent
Rivera, Jr.

(10) Patent No.: US 12,642,668 B2
(45) Date of Patent: Jun. 2, 2026

(54) PROSTHETIC IMPLANT REMOVAL TOOL AND TOOL SET

(71) Applicant: DePuy Ireland Unlimited Company, Ringaskiddy (IE)

(72) Inventor: Jose S. Rivera, Jr., Naples, FL (US)

(73) Assignee: DEPUY IRELAND UNLIMITED COMPANY, Ringaskiddy (IE)

( * ) Notice: Subject to any disclaimer, the term of this patent is extended or adjusted under 35 U.S.C. 154(b) by 880 days.

(21) Appl. No.: 17/387,805

(22) Filed: Jul. 28, 2021

(65) Prior Publication Data

US 2021/0353432 A1 Nov. 18, 2021

Related U.S. Application Data

(63) Continuation-in-part of application No. 17/127,006, filed on Dec. 18, 2020, now Pat. No. 11,938,032,
(Continued)

(51) Int. Cl.
*A61F 2/46* (2006.01)
*A61B 17/16* (2006.01)

(52) U.S. Cl.
CPC ........ *A61F 2/4607* (2013.01); *A61B 17/1668* (2013.01); *A61F 2002/4681* (2013.01)

(58) Field of Classification Search
CPC .... A61F 2/4603; A61F 2/4607; A61F 2/4619; A61B 17/155; A61B 17/164;
(Continued)

(56) References Cited

U.S. PATENT DOCUMENTS

| | | | |
|---|---|---|---|
| 4,222,382 A | 9/1980 | Antonsson et al. | |
| 4,736,738 A | 4/1988 | Lipovsek et al. | |
| | (Continued) | | |

FOREIGN PATENT DOCUMENTS

| | | | |
|---|---|---|---|
| GB | 2560956 A | 10/2018 | |
| JP | 2013523289 A | 6/2013 | |
| | (Continued) | | |

OTHER PUBLICATIONS

Japanese Office Action issued Jan. 31, 2024 in corresponding Japanese Patent Application No. 2021-572565, 7 pages.
(Continued)

*Primary Examiner* — Matthew J Lawson
(74) *Attorney, Agent, or Firm* — XSENSUS LLP

(57) ABSTRACT

Disclosed is a tool set and an associated method for removing a prosthetic implant. Although the tools in the tool set can be used to remove a variety of different prosthetic implants, it finds particular application in the removal of femoral implants. In one embodiment, both lateral and medial tools are utilized. The lateral tool includes a generally arcuate shape with upstanding sidewalls that define an arcuate interior. The lateral tool is thus dimensioned to follow the contour of the lateral side of a femoral implant. The medial tool includes opposing side walls that define an interior opening. The opening is sized to receive the neck of the femoral implant, thereby allowing the tool to closely follow the medial bone/implant interface. In another embodiment, a J-shaped tool and an L-shaped tool are utilized to cut below an undercut of an femoral implant. The tools in the tool set can work together or individually.

20 Claims, 29 Drawing Sheets

Related U.S. Application Data which is a continuation-in-part of application No. 16/431,879, filed on Jun. 5, 2019, now Pat. No. 11,191,651.

(60) Provisional application No. 63/202,053, filed on May 25, 2021, provisional application No. 63/199,654, filed on Jan. 14, 2021.

(58) Field of Classification Search
CPC .............. A61B 7/1604; A61B 17/1664; A61B 17/1668; A61B 17/1732; A61B 17/1735; A61B 7/1742; A61B 17/1742
See application file for complete search history.

(56) References Cited

U.S. PATENT DOCUMENTS

| | | | |
|---|---|---|---|
| 4,838,853 A | 6/1989 | Parisi | |
| 5,019,083 A | 5/1991 | Klapper et al. | |
| 5,167,619 A | 12/1992 | Wuchinich | |
| 5,257,995 A | 11/1993 | Umber et al. | |
| D344,801 S | 3/1994 | Hughes et al. | |
| 5,318,570 A * | 6/1994 | Hood ................. | A61B 17/8847 601/2 |
| 5,342,366 A | 8/1994 | Whiteside et al. | |
| 5,405,349 A * | 4/1995 | Burkinshaw ....... | A61B 17/1675 606/88 |
| 5,716,405 A | 2/1998 | Mittelman | |
| 5,820,315 A * | 10/1998 | Collard .............. | B23B 51/0426 408/209 |
| 5,885,301 A | 3/1999 | Young | |
| 5,961,522 A | 10/1999 | Mehdizadeh | |
| 6,126,664 A | 10/2000 | Troxell et al. | |
| 6,187,012 B1 | 2/2001 | Masini | |
| 6,790,211 B1 * | 9/2004 | McPherson ........... | A61F 2/4607 606/169 |
| 7,744,616 B2 | 6/2010 | O'Donoghue | |
| 7,935,118 B2 | 5/2011 | Vendrely et al. | |
| 8,545,507 B2 | 10/2013 | Vendrely et al. | |
| 9,603,720 B2 | 3/2017 | Kelley | |
| 9,730,705 B2 | 8/2017 | Smith et al. | |
| 9,867,628 B2 | 1/2018 | Macke | |
| 9,876,628 B2 | 1/2018 | Golitschek Edler Von Elbwart et al. | |
| 10,751,070 B2 | 8/2020 | Pendleton et al. | |
| 11,191,651 B1 * | 12/2021 | Rivera, Jr. ............ | A61F 2/4607 |
| 2002/0068941 A1 | 6/2002 | Hanson et al. | |
| 2002/0091387 A1 | 7/2002 | Hoogland | |
| 2003/0236525 A1 | 12/2003 | Vendrely et al. | |
| 2004/0162619 A1 * | 8/2004 | Blaylock ............. | A61F 2/30734 606/88 |
| 2005/0090829 A1 | 4/2005 | Martz et al. | |
| 2005/0251146 A1 | 11/2005 | Martz et al. | |
| 2007/0123893 A1 | 5/2007 | O'Donoghue | |
| 2008/0188878 A1 * | 8/2008 | Young .................. | A61B 17/144 606/171 |
| 2010/0069909 A1 * | 3/2010 | Taylor ................... | A61F 2/4607 606/82 |
| 2010/0100097 A1 | 4/2010 | Wong | |
| 2011/0004214 A1 | 1/2011 | Skaggs | |
| 2011/0288555 A1 | 11/2011 | Szanto | |
| 2012/0089147 A1 | 4/2012 | Kuczynski | |
| 2012/0283793 A1 | 11/2012 | Burroughs, III | |
| 2013/0226189 A1 | 8/2013 | Young | |
| 2014/0276835 A1 | 9/2014 | Tally | |
| 2014/0371750 A1 * | 12/2014 | Klein ................. | A61B 17/1604 606/79 |
| 2015/0039037 A1 | 2/2015 | Donner et al. | |
| 2015/0196402 A1 | 7/2015 | Kim | |
| 2016/0338751 A1 | 11/2016 | Kellar et al. | |
| 2018/0206859 A1 * | 7/2018 | Pendleton .......... | A61B 17/1637 |
| 2018/0221171 A1 | 8/2018 | Termanini et al. | |
| 2018/0280036 A1 | 10/2018 | Agunloye et al. | |
| 2019/0314043 A1 | 10/2019 | Sekel | |
| 2019/0336143 A1 * | 11/2019 | Wright ............... | A61B 17/1778 |
| 2020/0261247 A1 | 8/2020 | Stchur et al. | |
| 2021/0353432 A1 | 11/2021 | Rivera, Jr. | |
| 2023/0172622 A1 * | 6/2023 | Wright ............... | A61B 17/1604 606/84 |
| 2024/0108475 A1 * | 4/2024 | Rivera, Jr. ............ | A61F 2/4603 |

FOREIGN PATENT DOCUMENTS

| | | |
|---|---|---|
| JP | 2013208430 A | 10/2013 |
| JP | 2018525121 A | 9/2018 |
| WO | 92/22259 A2 | 12/1992 |
| WO | 2012006508 A2 | 1/2012 |
| WO | 2020/247064 A1 | 12/2020 |
| WO | 2022/140801 A2 | 6/2022 |

OTHER PUBLICATIONS

Extended European Search Report issued Aug. 5, 2022, in corresponding European Application No. 20817983.8.

International Search Report and Written Opinion mailed on Jun. 22, 2022, corresponding PCT/US 22/13102, 11 pages.

Rivera Surgical, "Watson Extraction System", YouTube demonstration, Oct. 23, 2020, available URL: https://www.youtube.com/watch?v=CrD5vsMujiA.

Chinese Office Action issued Jun. 13, 2022, in corresponding Chinese Application No. 202080054684.7.

Extended European search report issued on Jun. 15, 2023, in corresponding European patent Application No. 22740032.2, 8 pages.

Office Action issued on Dec. 30, 2022, in corresponding Chinese patent Application No. 202080054684.7 with partial English translation, 4 pages.

Brazilian Preliminary Office Action issued Jun. 25, 2024 in corresponding Brazilian Patent Application No. BR112021024631-2, 5 pages.

International Search Report for PCT/US/20/27692 with an International filing dale of Apr. 10, 2020, and mailed on Jul. 17, 2020.

U.S. Office Action issued Mar. 28, 2023 in co-pending U.S. Appl. No. 17/515,941.

U.S. Final Office Action issued Jun. 6, 2023 in co-pending U.S. Appl. No. 17/515,941.

U.S. Office Action issued Sep. 18, 2024 in co-pending U.S. Appl. No. 18/389,795.

U.S. Office Action issued Sep. 24, 2024 in co-pending U.S. Appl. No. 18/596,730.

U.S. Notice of Allowance issued Sep. 28, 2024 in co-pending U.S. Appl. No. 17/515,941.

Korean Office Action issued Jan. 21, 2025 in corresponding Korean Patent Application No. 2022-7000296, 9 pages.

Japanese Office Action issued Oct. 16, 2024 in corresponding Japanese Patent Application No. 2021-572565, 4 pages.

U.S. Office Action issued Feb. 13, 2025 in co-pending U.S. Appl. No. 17/628,453, 108 pages.

U.S. Final Office Action issued Jan. 31, 2025 in co-pending U.S. Appl. No. 18/389,795, 57 pages.

U.S. Notice of Allowance issued Apr. 25, 2025 in co pending U.S. Appl. No. 18/596,730, 95 pages.

International Search Report issued Mar. 30, 2022 in corresponding International Patent Application No. PCT/US22/12238, 1 page.

Korean Notice of Allowance issued May 26, 2025 in corresponding Korean Patent Application No. 10-2022-7000296, 4 pages.

Japanese Notice of Allowance issued Jun. 3, 2025 in corresponding Japanese Patent Application No. 2021-572565, 4 pages (with machine-generated translation).

U.S. Notice of Allowance issued Jun. 13, 2025 in co-pending U.S. Appl. No. 17/628,453, 82 pages.

Australian Examination Report issued Jul. 14, 2025 in corresponding Australian Patent Application No. 2020286413, 4 pages.

U.S. Notice of Allowance issued Jul. 17, 2025 in co-pending U.S. Appl. No. 17/628,453, 78 pages.

U.S. Nonfinal Office Action issued Jul. 9, 2025 in co-pending U.S. Appl. No. 18/389,795, 102 pages.

(56) References Cited

OTHER PUBLICATIONS

U.S. Notice of Allowance issued Aug. 12, 2025 in co-pending U.S. Appl. No. 18/596,730, 95 pages.
Japanese Office Action issued Aug. 19, 2025 in corresponding Japanese Patent Application No. 2022-563463, 10 pages.
Australian Examination Report issued Oct. 23, 2025 in corresponding Australian Patent Application No. 2020286413, 3 pages.
Brazilian Office Action issued Nov. 11, 2025 in Brazilian Patent Application No. BR112021024631-2, 6 pages.
Japanese Notice of Allowance issued Nov. 25, 2025 in Japanese Patent Application No. 2022-563463, 5 pages.
U.S. Notice of Allowance issued Dec. 2, 2025 in co-pending U.S. Appl. No. 18/389,795.
Indian Office Action issued Feb. 12, 2026 in corresponding Indian Patent Application No. 202317047243, 7 pages.
Indian Office Action issued Feb. 18, 2026 in corresponding Indian Patent Application No. 202247050290, 7 pages.

* cited by examiner

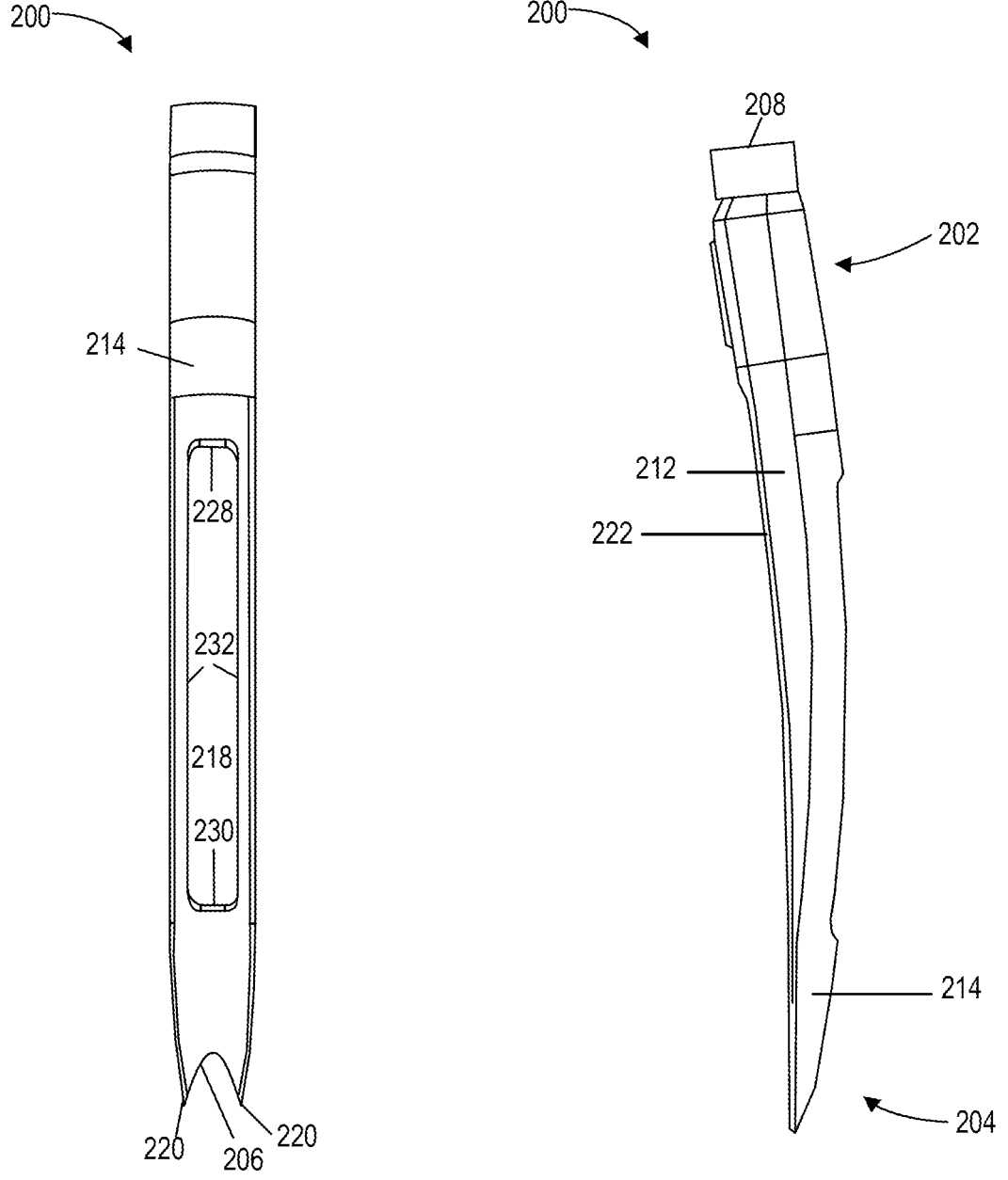
FIG. 24　　　FIG. 25

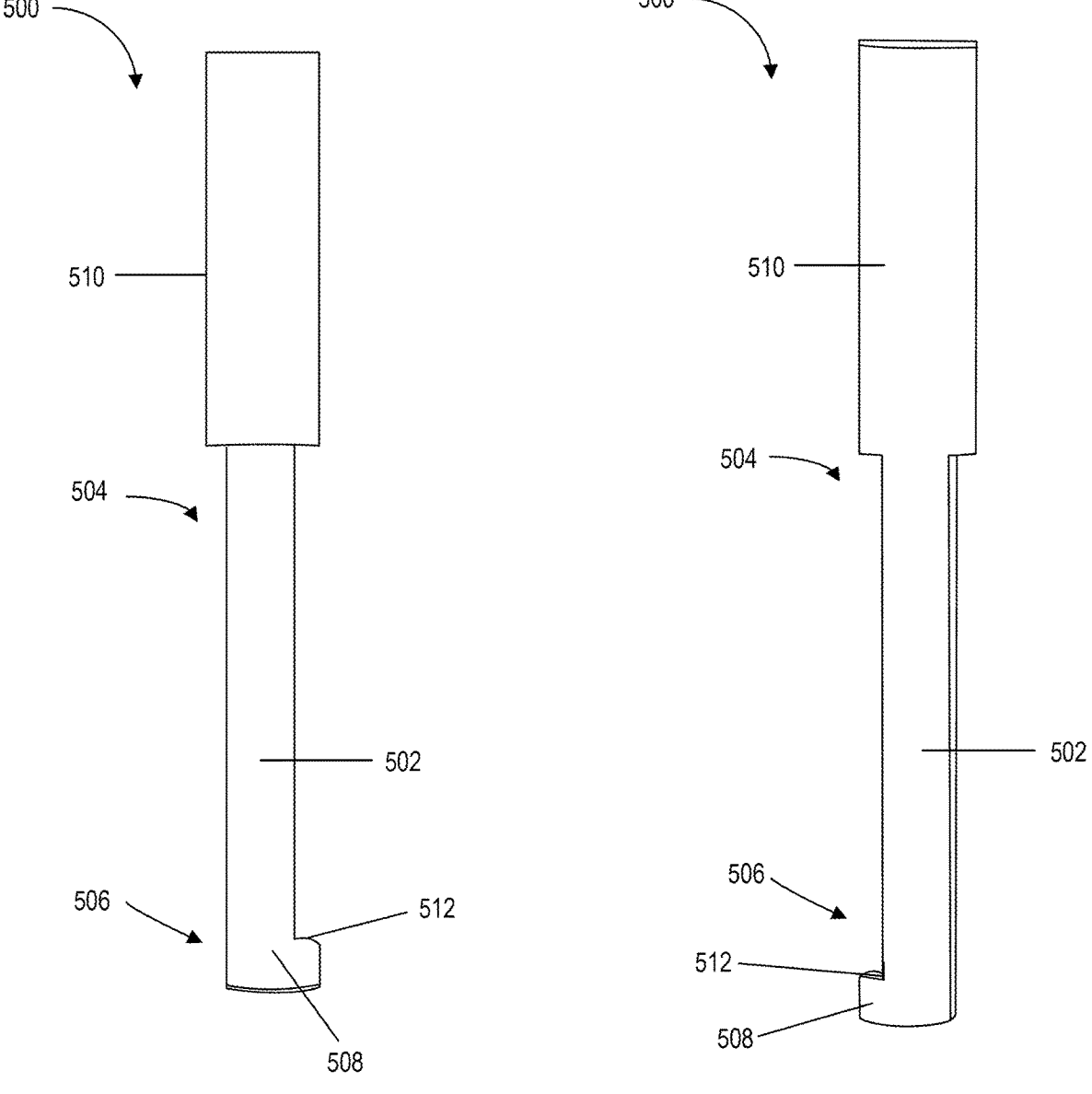
FIG. 41          FIG. 42

610

600

610

604

602

606

612

608

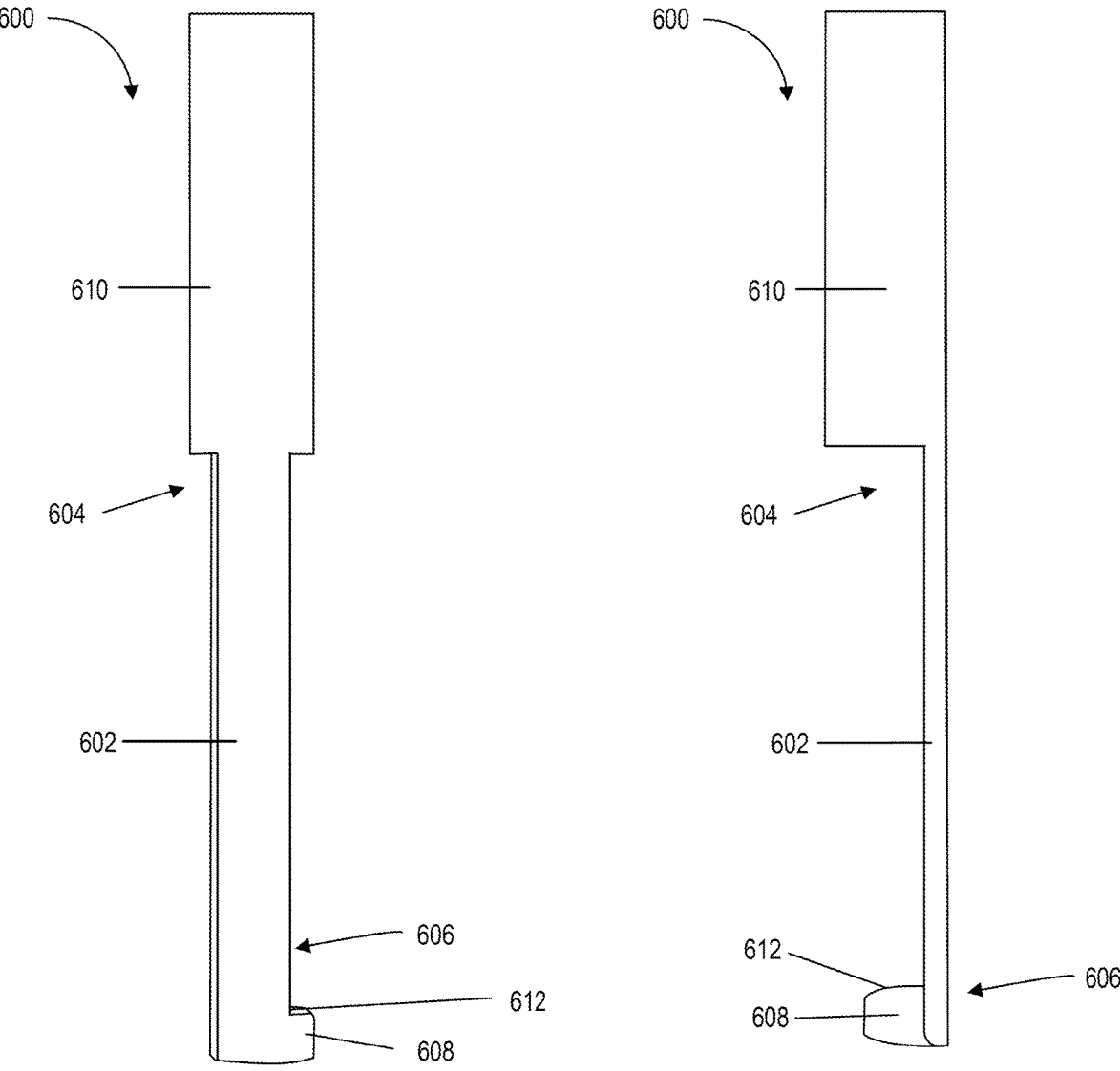
FIG. 47                FIG. 48

PROSTHETIC IMPLANT REMOVAL TOOL AND TOOL SET

CROSS REFERENCE TO RELATED APPLICATIONS

This application claims priority to provisional Application No. 63/199,654 filed on Jan. 14, 2021 and entitled "Prosthetic Implant Removal Tool and Associated Method" and provisional Application No. 63/202,053 filed on May 25, 2021 and entitled "Implant Removal Tool Set", and is a continuation-in-part of co-pending application Ser. No. 17/127,006 filed on Dec. 18, 2020 and entitled "Prosthetic Implant Removal Tool and Associated Method," which is a continuation-in-part of co-pending application Ser. No. 16/431,879 filed on Jun. 5, 2019 and entitled "Implant Removal Tool." The contents of these co-pending provisional and non-provisional applications are fully incorporated herein for all purposes.

TECHNICAL FIELD

This disclosure relates to a tool set for removing a prosthetic implant. More particularly, the present disclosure relates to tools and associated methods for minimizing bone loss during the removal of a prosthetic.

BACKGROUND

Joint arthroplasty is increasingly common in the United States and around the world. Arthroplasty can involve the complete or partial replacement of hips, knees, or shoulders. Of these, hip replacements are the most common form of surgery. During a hip replacement, the surgeon replaces the socket of the hip bone, known as the acetabulum, with an acetabular cup. The head of the femur is also replaced with a femoral implant. Femoral implants include a stem that is inserted into the superior end of the femur and an angled neck that extends upwardly. The neck mimics the natural neck of the femur and provides an attachment point for a head to be attached. These implants include coatings and texturing to promote bone growth to affix the implant to the femur and hip socket.

Most hip replacements last for approximately 25 years. After this time the acetabular cup and femoral implants may fail and need to be repaired or replaced. As life expectancy in general increases, people are living with artificial hips for longer periods of time. As a result, hip revision surgeries are on the rise. Hip revisions surgeries can be complicated and often pose more risk than the original hip replacement. During revision surgeries surgeons attempt to remove the existing implants while minimizing damage to surrounding bone and tissue. This is often a difficult task as implants are designed to join with the surrounding bone over time. Minimizing the loss of this bone during a revision helps the new implant to be properly affixed. It also reduces the length and cost of the revision surgery and further reduces recovery time. Efforts have been made over the years to provide tools that aid in the efficient removal of a prosthetic.

One example of this is disclosed in U.S. Pat. No. 9,867, 628 to Macke. Macke relates to a method for the extraction of medical implants. In accordance with the method, a surgical cutting guide is attached to an implanted prosthesis. An osteotome is directed through a slot in the surgical cutting guide to a specified location at the interface between the prosthesis and the bone. The prosthesis is dislodged using the osteotome. The osteotome is then withdrawn through the slot. The slot can include a curvature to assist with minimizing bone loss.

Another implant removal tool is disclosed in U.S. Pat. No. 6,187,012 to Masini. Masini discloses a guide means for directing a cutting tool into the interface between a prosthesis and the surrounding bone. The guide means is used to bring about a more controlled separation and removal of the prosthesis. The guide may be placed on the prosthesis itself or it may be placed on a separate component. In the case of a femoral implant, the guide can include tracks, channels, or groves that are oriented along the stem of the implant.

U.S. Pat. No. 5,257,995 to Umber discloses an apparatus for removing a prosthesis from a bone. The apparatus includes a cutting tool having a cutting tip and an elongated shank that is designed to allow significant lateral flexing. A motor is included to provide rotational motion to the cutting tool. A handle is also provided that is designed to be held in the hand opposite the cutting tool. The handle includes a bearing carrier with a hole for receiving the shank of the cutting tool. The surgeon manipulates the handle and cutting tool to cut a perimeter around the prosthesis.

A further example is illustrated in U.S. Pat. No. 10,751, 070 to Pendleton. Pendleton discloses a device that has at least one blade connected to a handle. The shape of the blade conforms to a portion of an implant so that a cutting tip of the blade can be positioned in a desired position relative to the implant and the femur. Force is applied to the handle so that the cutting tip of the blade cuts through bone growth from the femur into the implant.

Although the background art illustrates various devices and techniques for removing prosthetics, all suffer from significant drawbacks. Namely, the devices of the background art rely heavily upon the technique of the surgeon and do not include tools that adequately accommodate the shape of the prosthetic being removed or that otherwise minimizes bone loss. The implant removal tool of the present disclosure is aimed at overcoming these and other shortcomings present in the background art.

SUMMARY

In accordance with the present disclosure, there is provided a tool for removal of a femoral implant. The tool comprises a proximal end; a proximal connector near the proximal end; a distal end having a leading edge; a lateral wall that is arcuate, allowing the distal end to penetrate into a femur substantially closely along a lateral side of the femoral implant; and side edges extending from the proximal end to the distal end and configured for cutting.

Also in accordance with the present disclosure, there is provided a tool for removal of a femoral implant. The tool comprises a proximal end; a proximal connector near the proximal end; a distal end having a leading edge; and a hook connected to the distal end, wherein all edges of the hook are configured for cutting.

Further in accordance with the present disclosure, there is provided a tool set for removal of a femoral implant. The tool set comprises at least one lateral tool; at least one medial tool; a J-shaped tool; or an L-shaped tool. The at least one lateral tool comprises a lateral tool proximal end; a lateral tool proximal connector near the lateral tool proximal end; a lateral tool distal end having a lateral tool leading edge; a lateral tool lateral wall that is arcuate, allowing the lateral tool distal end to penetrate into a femur substantially closely along a lateral side of the femoral implant; and lateral tool side edges extending from the lateral tool proximal end to the lateral tool distal end configured for cutting. The at least one medial tool comprises a medial tool proximal end; a medial tool proximal connector near the medial tool proximal end; a medial tool distal end having a medial tool leading edge; a medial tool lateral wall that is arcuate; side edges extending from the proximal end to the distal end configured for cutting; and at least one opening located in the medial tool lateral wall allowing a femoral implant to partially pass through as the medial tool advancing into a femur. The J-shaped and the L-shaped tool each comprises a side tool proximal end; a side tool proximal connector near the side tool proximal end; a side tool distal end having a side tool leading edge; and a hook connected to the side tool distal end, wherein all edges of the hook are configured for cutting.

BRIEF DESCRIPTION

For a more complete understanding of the present disclosure and its advantages, reference is now made to the following descriptions, taken in conjunction with the accompanying drawings, in which:

FIG. 24 is a back view of the lateral implant removal tool shown in FIG. 22.

FIG. 25 is a side view of the lateral implant removal tool shown in FIG. 22.

FIG. 41 is a front view of the J-shaped tool shown in FIG. 39.

FIG. 42 is a back view of the J-shaped tool shown in FIG. 39.

FIG. 47 is a back view of the L-shaped tool shown in FIG. 44.

FIG. 48 is a side view of the L-shaped tool shown in FIG. 44.

Similar reference numerals refer to similar parts throughout the several views of the drawings.

DETAILED DESCRIPTION

The present disclosure relates to tools and associated methods for removing a prosthetic implant. Although the tool can be used to remove a variety of different prosthetic implants, it finds particular application in the removal of femoral implants. In one embodiment, both lateral and medial tools are utilized. In some embodiments, at least one lateral tool is utilized with at least one of a medial tool or medial tools, a J-shaped tool, or an L-shaped tool. In an illustrative non-limiting embodiment, the lateral tool includes a generally arcuate shape with upstanding sidewalls that define an arcuate interior. The lateral tool is thus dimensioned to follow the contour of the lateral side of a femoral implant. The medial tool, in one embodiment, includes opposing side walls that define an interior opening. The opening is sized to receive a neck of the femoral implant, thereby allowing the tool to closely follow the medial bone/implant interface. The details of these tools, and the manner in which they can be employed, are discussed in greater detail hereinafter.

Figure 12:
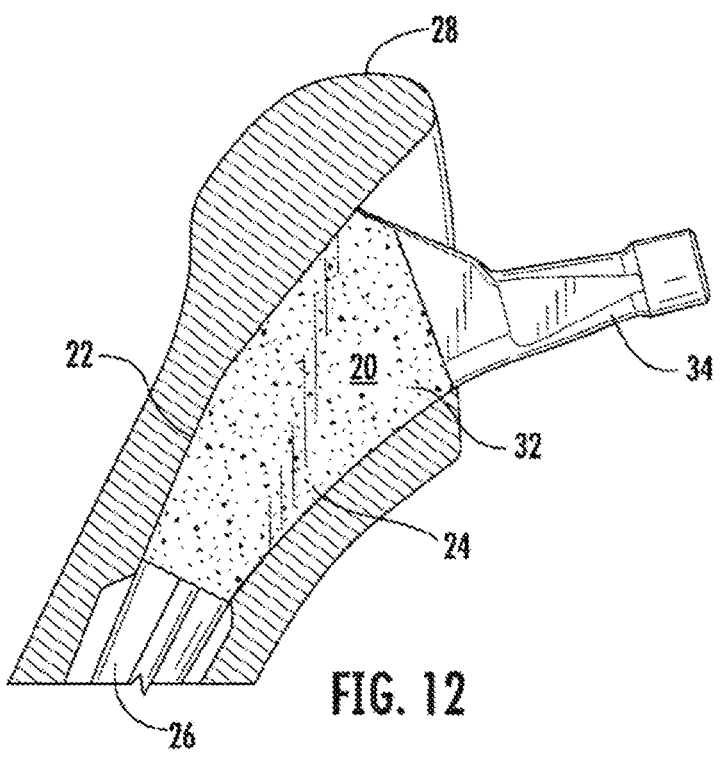
FIG. 12 illustrates a femoral implant prior to insertion of a lateral or medial tool.
Figure 13:
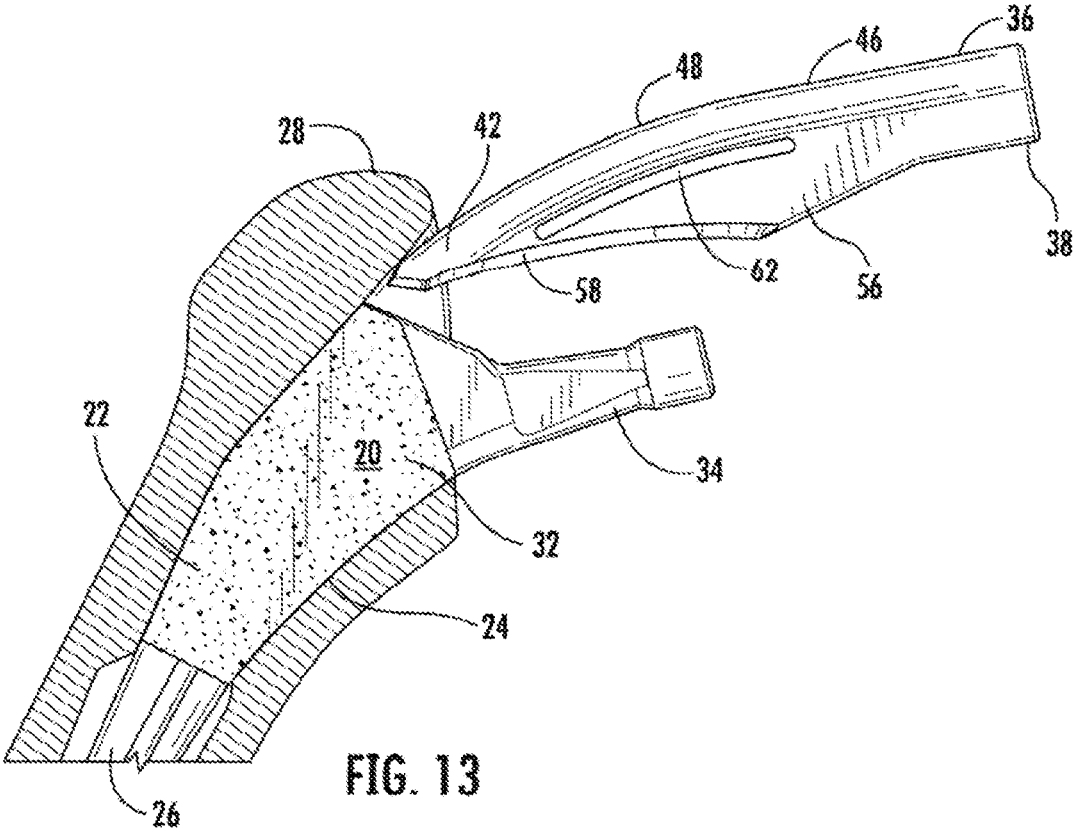
FIGS. 13-15 illustrate the insertion of the lateral implant removal tool of FIGS. 1-2.
Figures 14, 15:
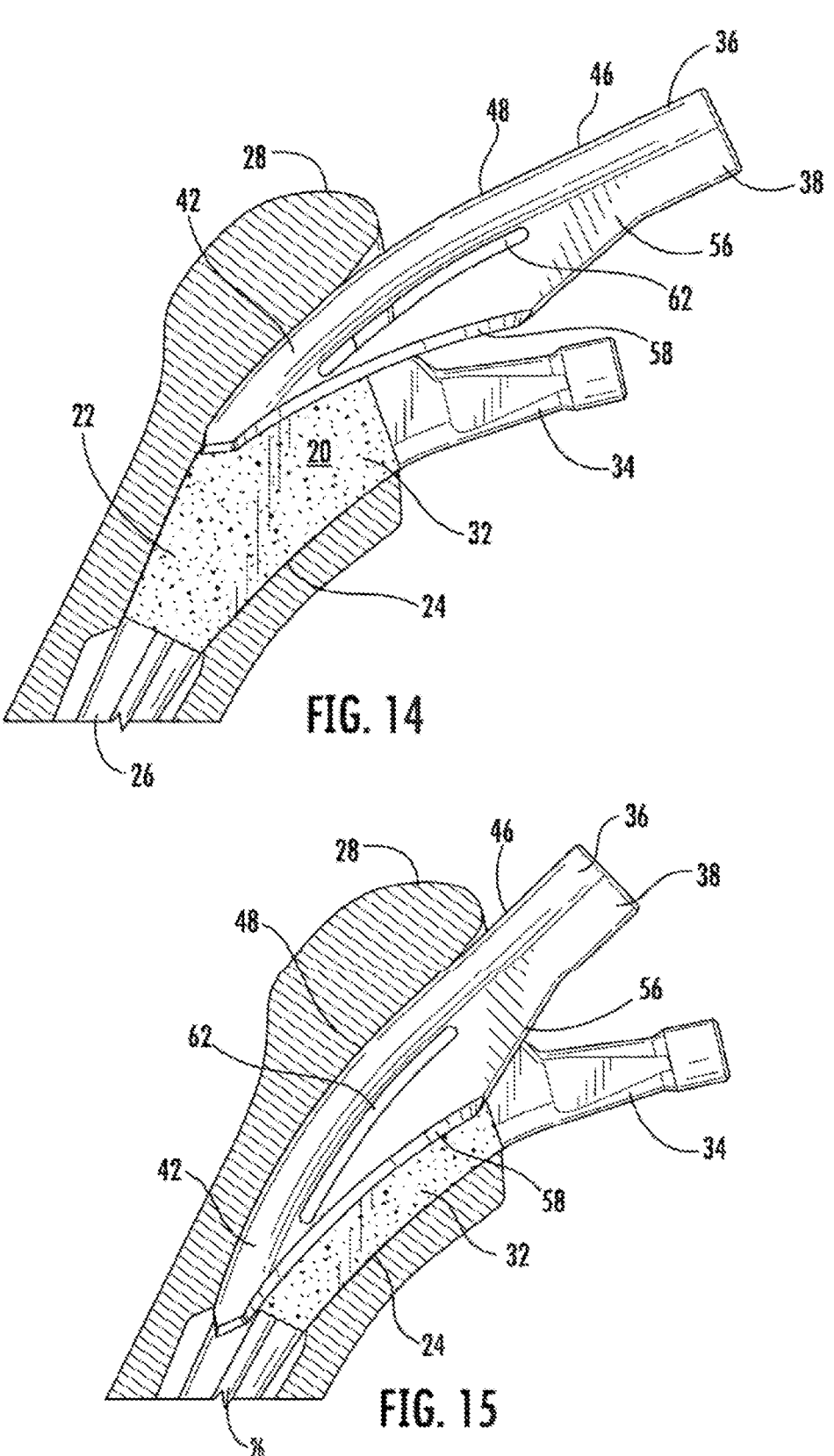
Figure 16:
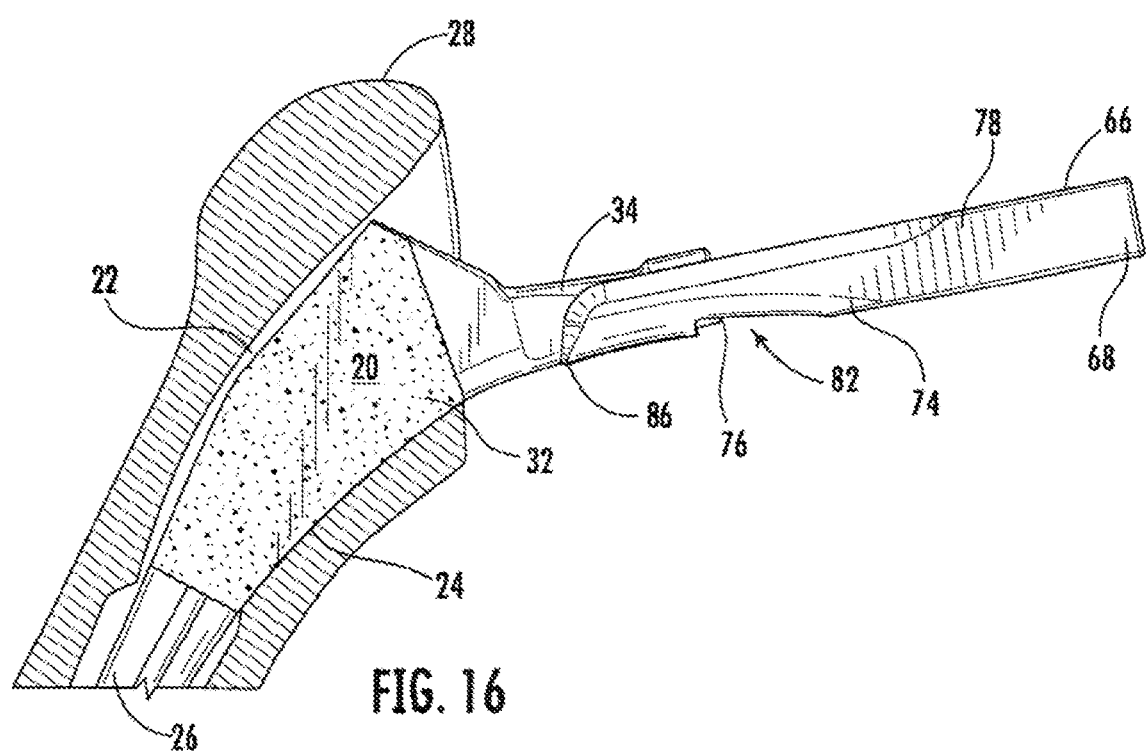
FIG. 16-17 illustrate the insertion of the medial implant removal tool of FIG. 3-5.
Figure 17:
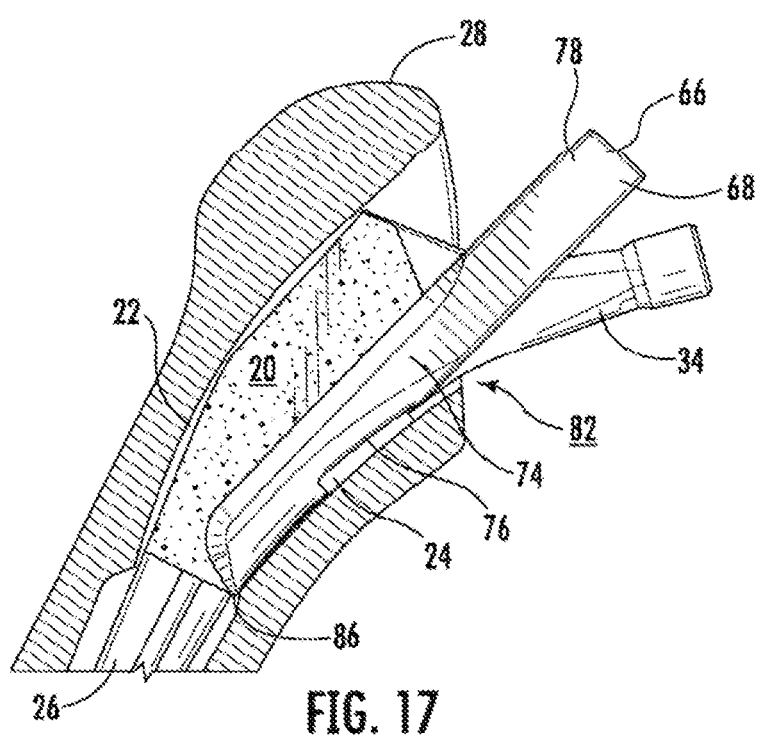

The disclosed tools are specifically configured to release an implanted prosthesis by closely following the bone/implant interface. The tools can be employed to remove a wide variety of different prosthetics, such as shoulder and hip implants. However, in the illustrated embodiments, the tools are used to cut around, dislodge, and remove a femoral implant 20 shown in FIG. 12. As depicted in FIG. 12, femoral implant 20 generally includes a lateral (or outer) side 22 and a medial (or inner) side 24. Implant 20 further include a stem 26 that is inserted into a superior end of a femur bone 28. Various coatings and texturing can be employed for promoting bone growth and the grafting of implant 20 to femur 28. As illustrated, implant 20 includes a textured portion 32 at its upper portion where bone growth and proper affixation are important. Femoral implant 20 also includes a neck 34 that is angled with respect to the body of implant 20. A head (not shown) is then secured to the end of neck 34, with the head ultimately being fitted into an acetabular cup (not shown).

Lateral Implant Removal Tool

Figure 1:
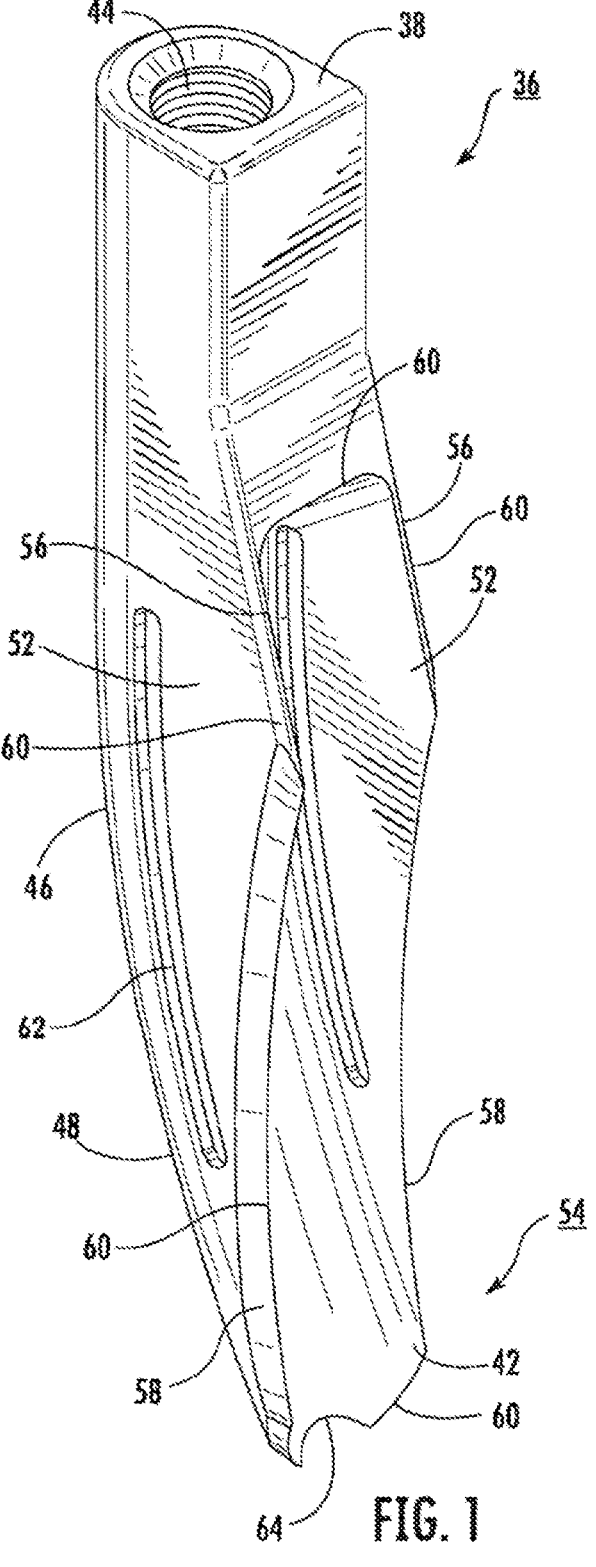
FIG. 1 is a perspective view of a lateral implant removal tool in accordance with some embodiments of the present disclosure.
Figure 2:
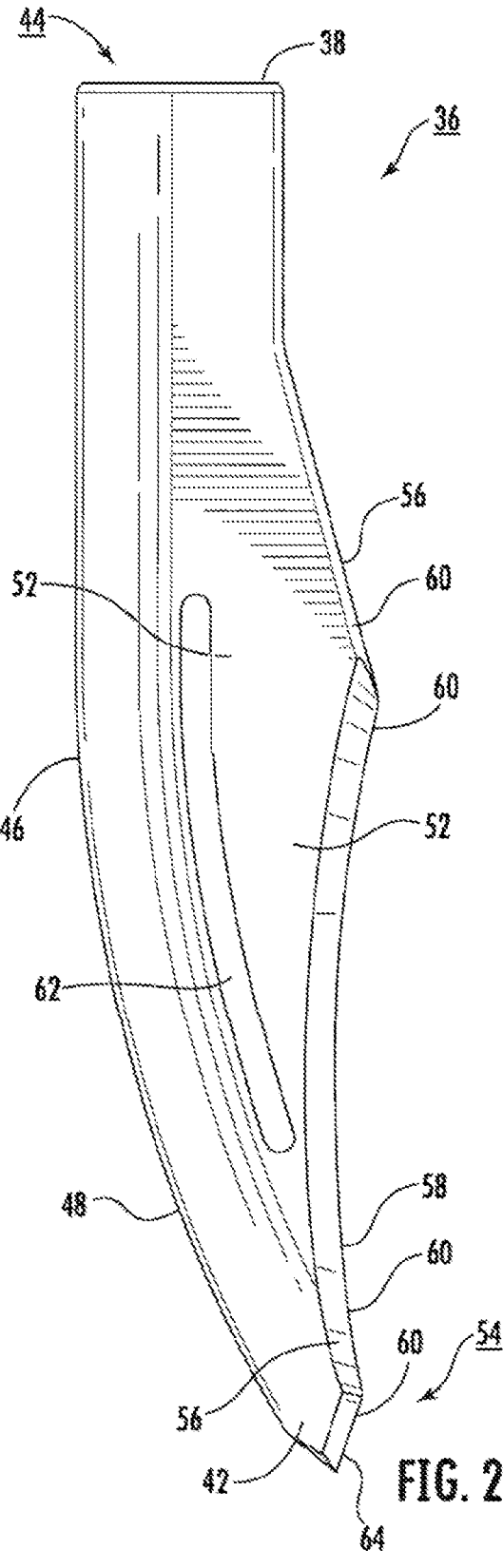
FIG. 2 is a side view of the lateral implant removal tool in accordance with some embodiments of the present disclosure.

With reference to FIGS. 1-2, a lateral tool 36 includes proximal and distal ends (38 and 42), with distal end 42 forming a leading edge that is inserted into femur 28. In order to allow tool 36 to be connected to an impact hammer (FIGS. 20-21), proximal end 38 includes a threaded aperture 44. It is also possible to couple tool 36 to the impact hammer via a quick release mechanism. The use of the impact hammer is described in greater detail hereinafter. Although the size and shape of femoral implants vary, often times lateral side 22 is curved to match the contour of femur 28. As such, lateral tool 36 includes a lateral wall 46 with an arcuate extent 48. Lateral tool 36 further includes opposing side walls 52. A curved or arcuate interior portion 54 is defined in the area between the opposing side walls 52. The shape and geometry of tool 36 may be changed to accommodate different types of prosthetics.

In one embodiment, each side wall 52 of lateral tool 36 includes a first angled extent 56 and a second curved extent 58. As illustrated, angled extent 56 is located nearer to proximal end 38 of tool 36 while curved extent 58 is located at distal end 42 of tool 36. Curved extents 58 of tool 36 are preferably angled and sharpened. All edges 60 surrounding interior portion 54 may be sharpened to facilitate insertion of tool 36. These sharpened edges 60 cut the bone growth along the bone/implant interface and otherwise allow for the insertion of tool 36. In order to allow the surgeon to gauge how far tool 36 has been inserted, a window 62 can be formed within one or both of the side walls 52. Distal end 42 of tool 36 optionally includes a curved and sharpened leading edge 64. Sharpened leading edge 64 and sharpened edges 60 allow lateral tool 36 to be inserted as closely as possible along the interface between the femur and implant. This, in turn, allows for efficient removal of femoral implant 20.

Medial Implant Removal Tool

Figures 3, 4, 5:
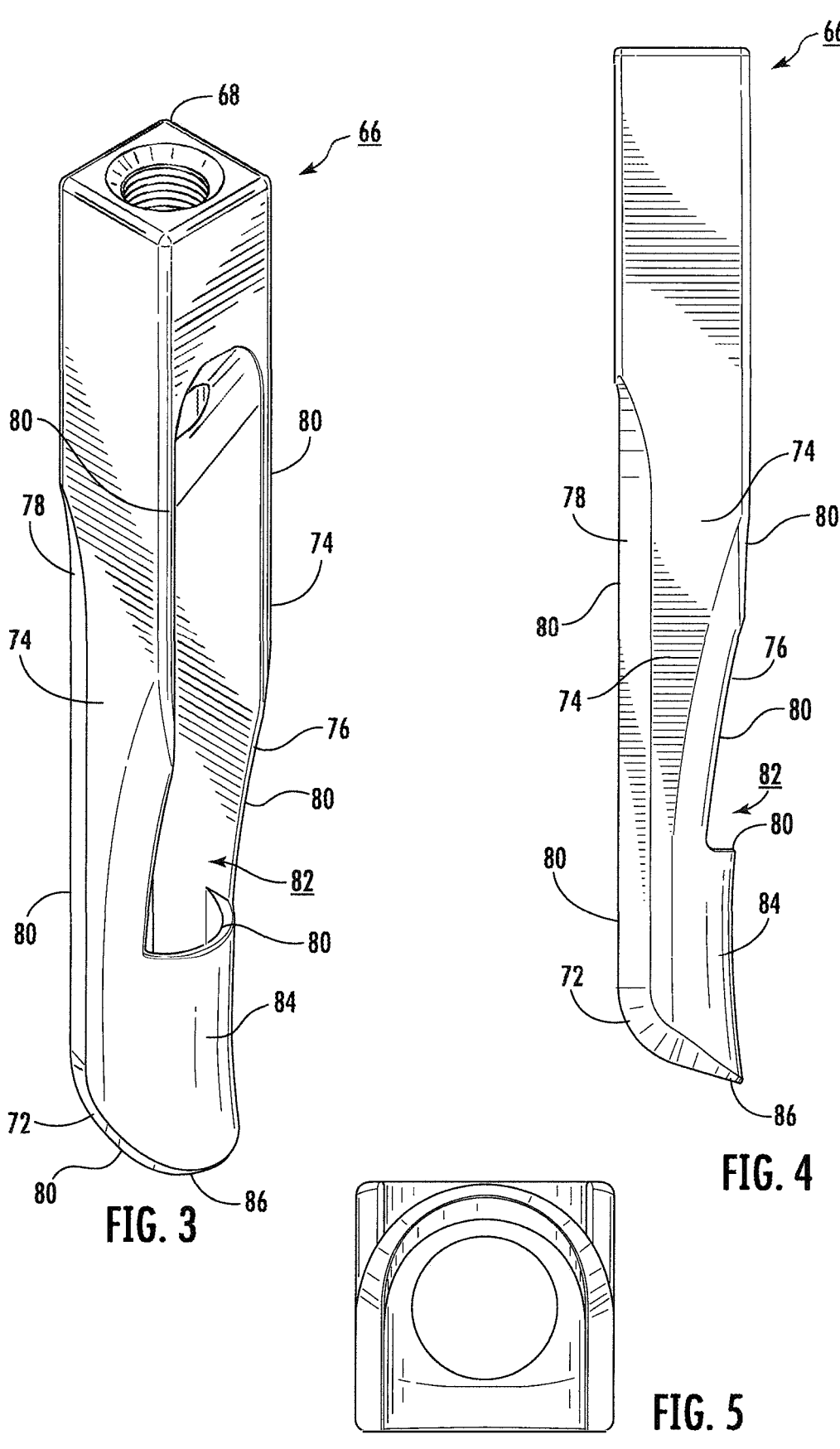
FIG. 3 is a perspective view of a medial implant removal tool in accordance with some embodiments of the present disclosure.
FIG. 4 is a side view of the medial implant removal tool in accordance with some embodiments of the present disclosure.
FIG. 5 is a bottom view of the medial implant removal tool in accordance with some embodiments of the present disclosure.

With reference to FIGS. 3-5, a medial tool 66 includes proximal and distal ends (68 and 72) as well as opposing side walls 74. Side walls 74 are defined by inner and outer edges (76 and 78), and in a preferred embodiment, outer edges 78 of walls 74 are sharpened. However, unlike lateral tool 36, medial tool 66 is not closed. Rather, medial tool 66 includes a generally central opening 82. The purpose of opening 82 is described hereinafter. All of inner and outer edges 80 surrounding central opening 82 are preferably sharpened. A U-shaped trough 84 with a sharpened leading edge 86 is formed at distal end 72 of medial tool 66. Medial tool 66 is adapted to be inserted between femur 28 and medial side 24 of femoral implant 20. All of sharpened edges 80 assist with insertion, including outer edges 78, inner edges 76, and leading edge 86. Furthermore, neck 34 of femoral implant 20 is allowed to extend through opening 82 of medial tool 66. In this regard, opening 82 is specifically sized to accommodate neck 34 and end of implant 20. The sharpened edges surrounding opening 82 allows tool 66 to cut along the anterior and posterior sides as well as the medial aspect of implant 20.

In another exemplary embodiment, as depicted in FIGS. 3-4, side walls 74 can have different length to make the overall length of medial tool 66 accommodate different implants.

Method of Using Lateral and Medial Tools

Figure 20:
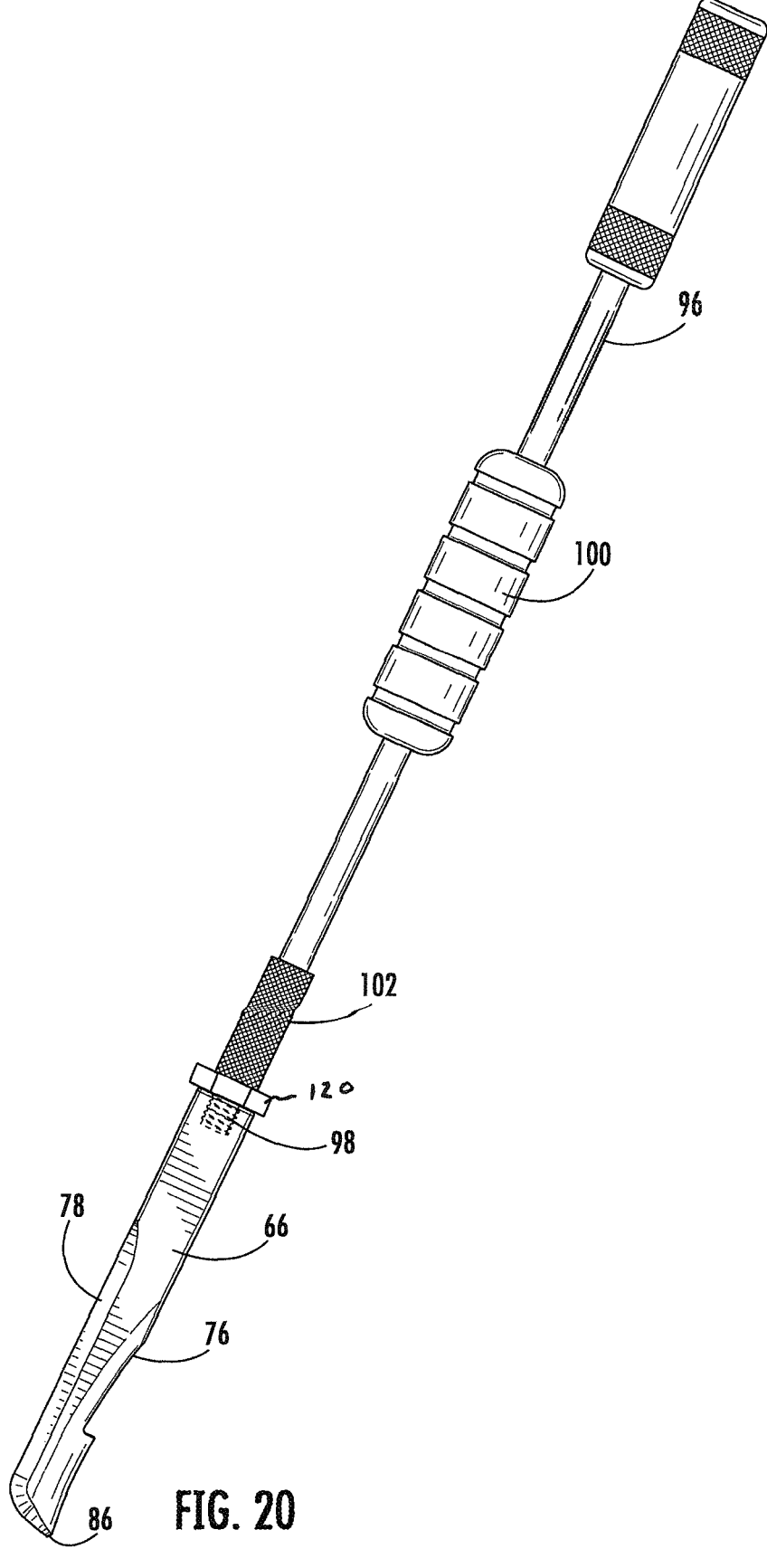
FIG. 20 is a view of an impact hammer secured to the medial tool of FIG. 3-5.
Figure 21:
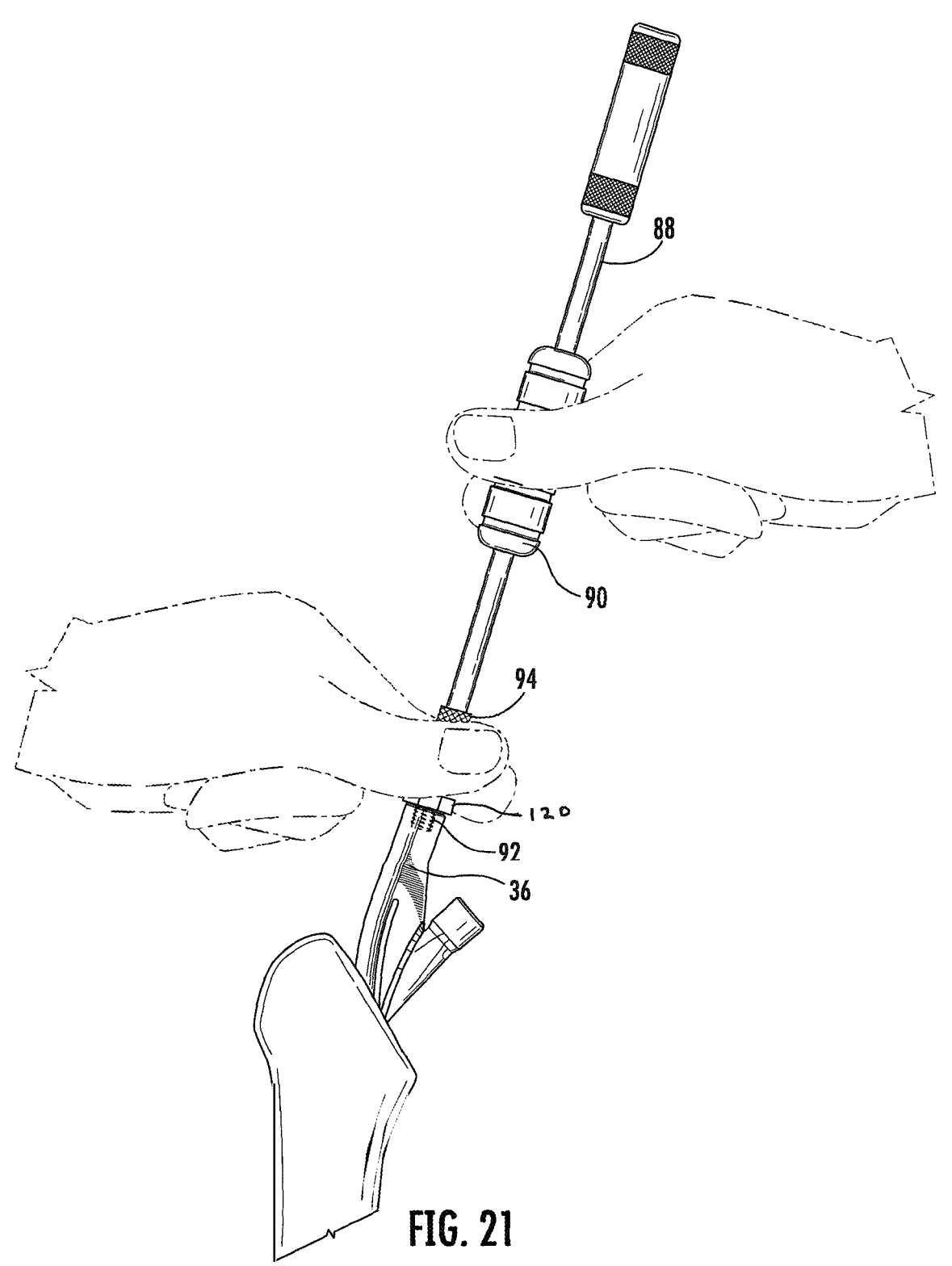
FIG. 21 is a view of an impact hammer being used to insert the lateral tool of FIG. 1-2.

A method of using lateral tools 36 and medial tool 66 is next described in connection with FIGS. 13-19. Both lateral and medial tools 36 and 66 can be used in conjunction with one another to remove femoral implant 20. However, the present disclosure is not limited to the use of both tools (36 and 66) and advantages disclosed herein can be realized by using either tool 36 or 66 individually. Each tool is inserted into the bone via an associated impact tool (88 and 96) (FIGS. 20-21). More specifically, a first impact tool 88 (FIG. 21) includes a threaded extent 92 that is secured to threaded aperture 44 of lateral tool 36. A nut 120 can be secured immediately above threaded extent 92 to prevent unintended rotation of impact tool 88 relative to lateral tool 36. Impact tool 88 includes a textured extent 94 that allows the surgeon to manipulate lateral tool 36 during insertion. The surgeon uses first impact tool 88 to guide the leading edge 64 and curved extents 58 of lateral tool 36 into femur 28. A weighted slide 90 is used as a hammer to apply force to the top of lateral tool 36. During this insertion of lateral tool 36, bone growth between the femoral implant 20 and femur 28 is cut.

Second impact tool 96 (FIG. 20) is substantially similar to the first impact tool 88 and is likewise used to position and insert medial tool 66. Namely, second impact tool 96 allows leading edge 86 and outer and inner edges (78, 76) of medial tool 66 (as well as all edges 80 surrounding opening 82) to cut bone growth between femoral implant 20 and femur 28 during the process of insertion. Second impact tool 96 likewise includes a threaded extent 98, a sliding weight 100, and a guide 102. Each impact tool (88, 96) can be manually inserted or can optionally be inserted via a pneumatic hammer or other striking tool.

Figure 18:
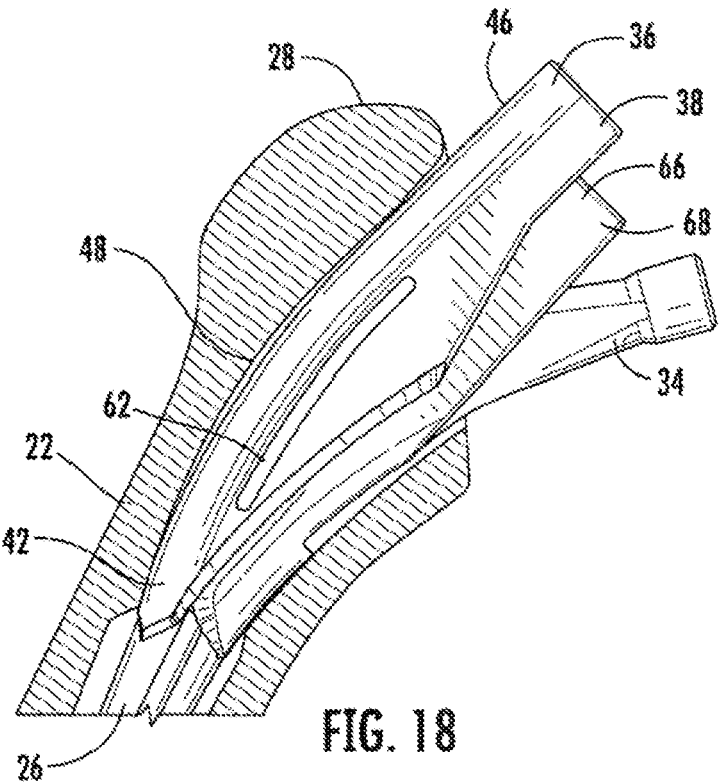
FIG. 18 illustrates the full insertion of both the lateral and medial tools.
Figure 19:
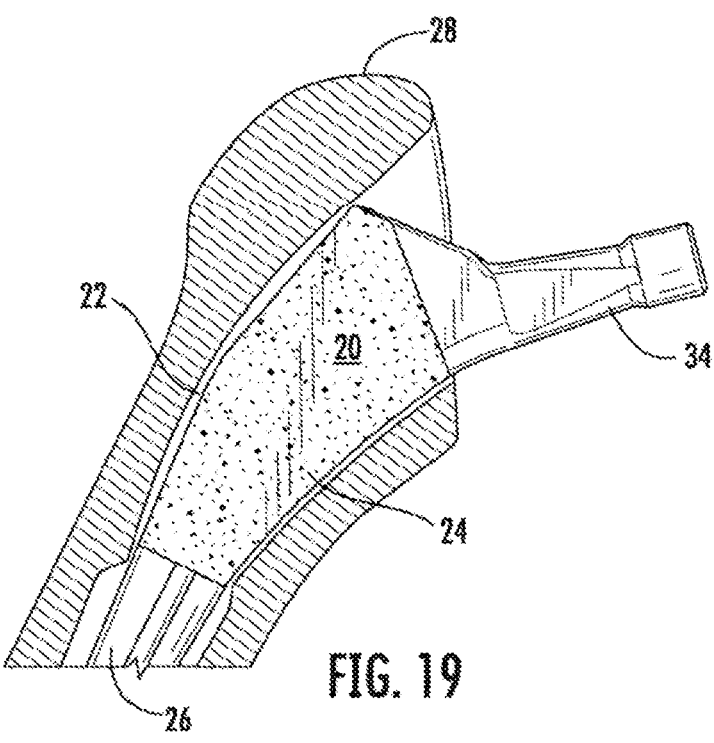
FIG. 19 illustrates the femoral implant following the removal of the lateral and medial tools.

As described, the lateral and medial implant removal tools (36 and 66) can be used in conjunction with one another. It is preferred that lateral tool 36 is inserted and removed prior to the insertion and removal of medial tool 66. FIG. 18 illustrates that in the preferred embodiment, lateral and medial tools (36 and 66) are inserted into femur 28 such that curved extents 58 of lateral tool 36 overlap outer edges 78 of medial tool 66.

The overlapping edges (58 and 78) ensure that all bone growth immediately surrounding implant 20 is removed. This ensures the efficient removal of implant 20 with minimal bone loss.

Alternative Embodiments of Medial Tool

Figures 6, 7, 8:
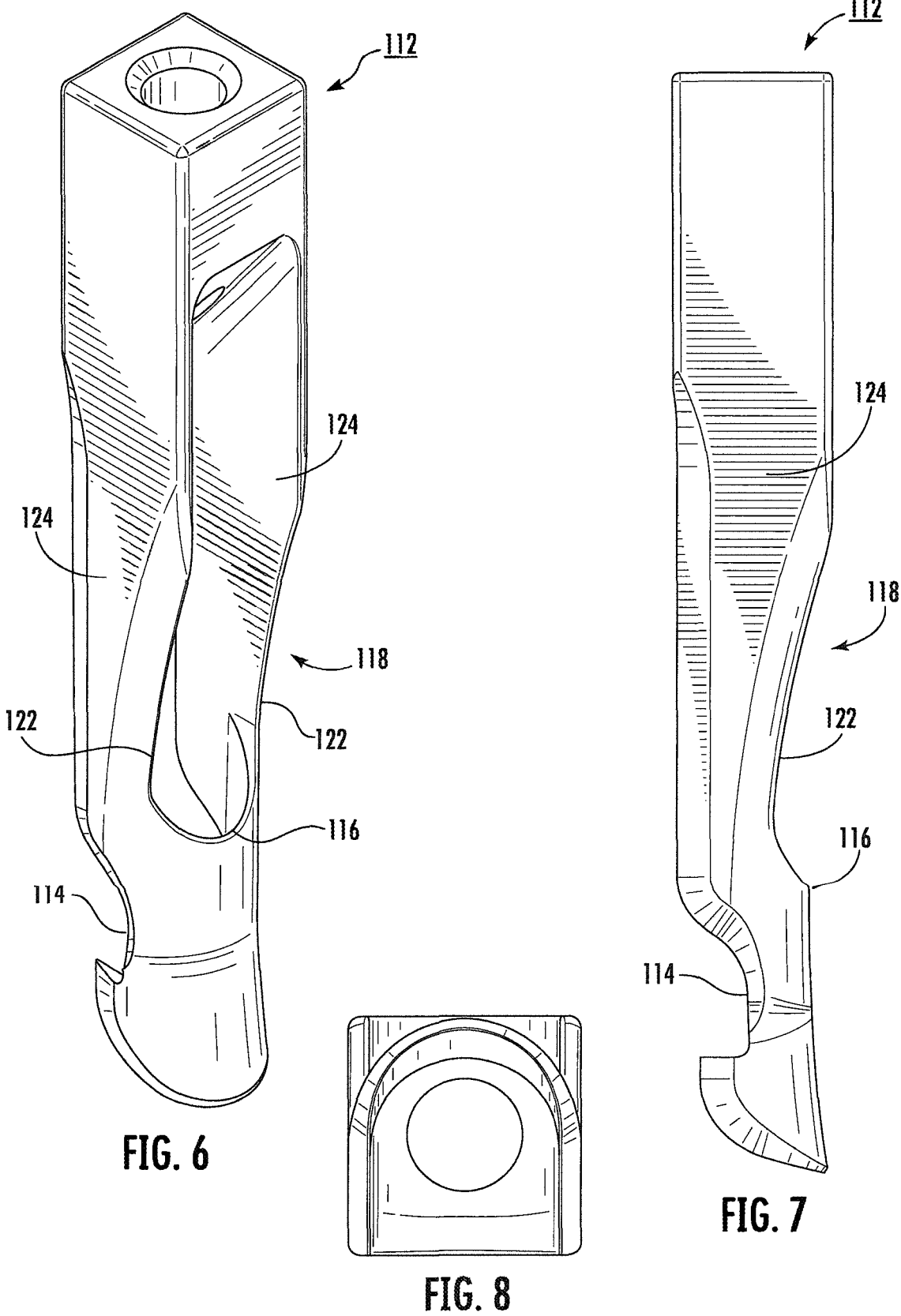
FIG. 6 is a perspective view of an alternative embodiment of the medial implant removal tool.
FIG. 7 is a side view of the alternative embodiment of the medial implant removal tool.
FIG. 8 is a bottom view of the alternative embodiment of the medial implant removal tool.

An alternative embodiment of a medial tool 112 is depicted in FIGS. 6-8. Tool 112 is generally the same as medial tool 66 (FIGS. 3-4), but includes a side cut out 114 leading to a narrower distal size when compared to the opening of 118. Medial tool 112 also includes an opening 118 to accommodate different neck geometries and has a lower rounded and sharpened edge 116. Medial tool 112 also includes opposing side walls 124 with inner sharpened edges 122. Side walls 124 can have a different length to make the overall length of medial tool 66 accommodating different implants.

Alternative Embodiments of Lateral Tools

Figures 9, 10:
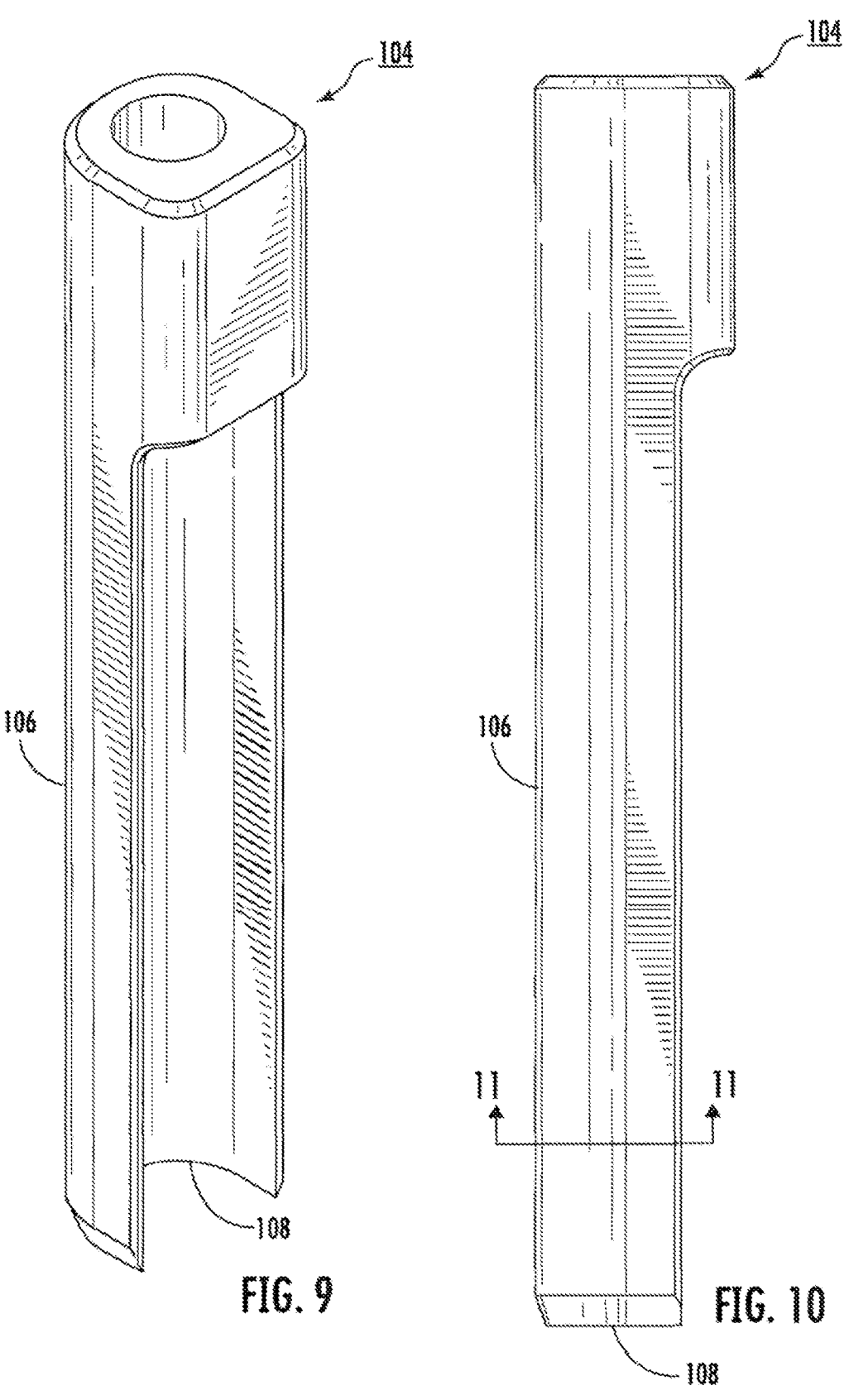
FIG. 9 is a perspective view of an alternative embodiment of the lateral implant removal tool.
FIG. 10 is a side view of the alternative embodiment of the lateral implant removal tool.
Figures 11, 11A, 11B:
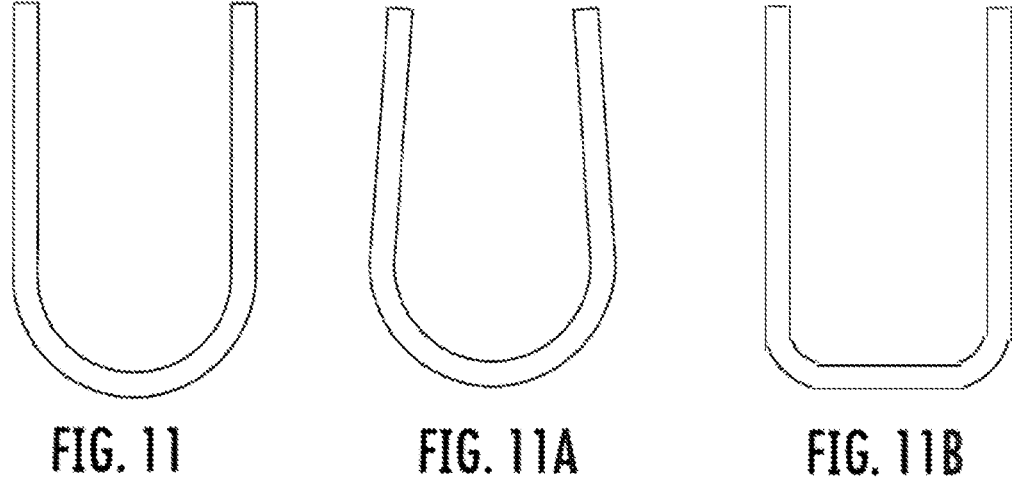
FIG. 11 is a sectional view of the alternative embodiment of the lateral implant removal tool taken along line 11-11 of FIG. 10.
FIGS. 11A-11E are alternative embodiments showing different cross sections of the lateral implant removal tool of FIG. 10, each of which being taken along section line 11-11.
Figures 11C, 11D, 11E:
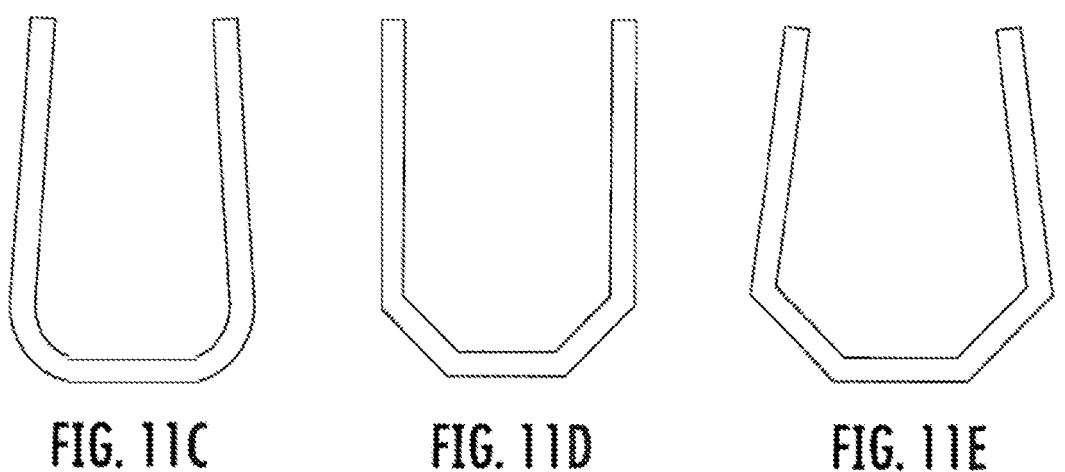

FIGS. 9 and 10 depict an alternative embodiment of a lateral tool as a lateral tool 104. Lateral tool 104 is the same in most respects as lateral tool 36. Lateral tool 104 includes a generally straight back wall 106 and a leading edge 108, more curved than leading edges 60 and 64 of lateral tool 36. This geometry may be preferred for the lateral tool depending upon the shape and size of the implant being removed. FIGS. 11 and 11A-11E illustrate a U-shaped cross section that makes up the body of lateral tool 104. However, any of a variety of cross-sectional shapes can be used. FIGS. 11 and 11A-11E illustrate some possible cross-sectional shapes for the lateral tool.

FIGS. 22-26 depict an alternative embodiment of a lateral tool as a lateral tool 200. Lateral tool 200 includes a proximal end 202 and a distal end 204, with distal end 204 forming a leading edge 206 for inserting into a femur. Proximal end 202 includes a proximal connector 208 and may include an indicia 210. Two opposing side walls 212 extending from proximal end 202 to distal end 204, and a lateral wall 214 extending from proximal end 202 to distal end 204, provide lateral tool 200 with a generally U-shaped or C-shaped cross section at most locations perpendicular to a longitudinal direction. Two opposing side walls 212 may be substantially parallel to each other. The inside surfaces of opposing side walls 212 and lateral wall 214 define an interior area 216, having a generally arcuate shape. In some embodiments, there may be an opening 218 in lateral wall 214. Opening 218 may be entirely in lateral wall 214, or partially in lateral wall 214 and partially in side walls 212. At some locations along the longitudinal direction, opening 218 may effectively remove lateral wall 214 and leave only side walls 212 or portions of side walls 212.

As shown in FIG. 22-25, leading edge 206 may have a curvature and two pointed ends 220. Leading edge 206 may be sharpened, rounded, or blunt.

In order to allow lateral tool 200 to be connected to an impact hammer, such as shown in FIGS. 20-21, proximal connector 208 may include a threaded aperture, a friction-fit connection, a twist lock, or other connector that allows for releasable connection to an impact hammer. In other aspects, proximal connector 208 may allow for releasable connection to a handle or other instruments, such as a vibration generating device. Proximal connector 208 may also include a quick release mechanism or a more permanent securement mechanism.

Figures 22, 23:
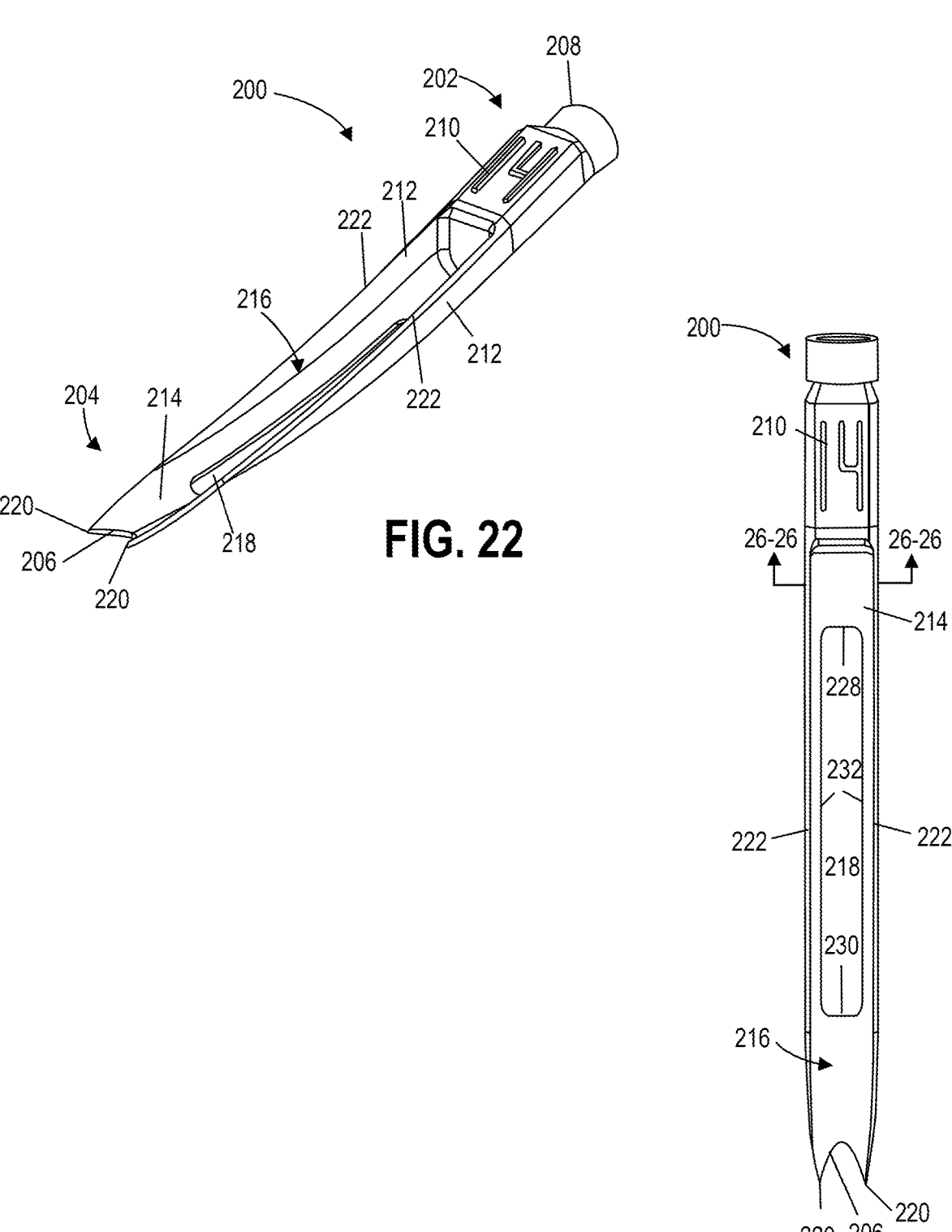
FIG. 22 is a perspective view of another alternative embodiment of the lateral implant removal tool.
FIG. 23 is a front view of the lateral implant removal tool shown in FIG. 22.
Figure 26:
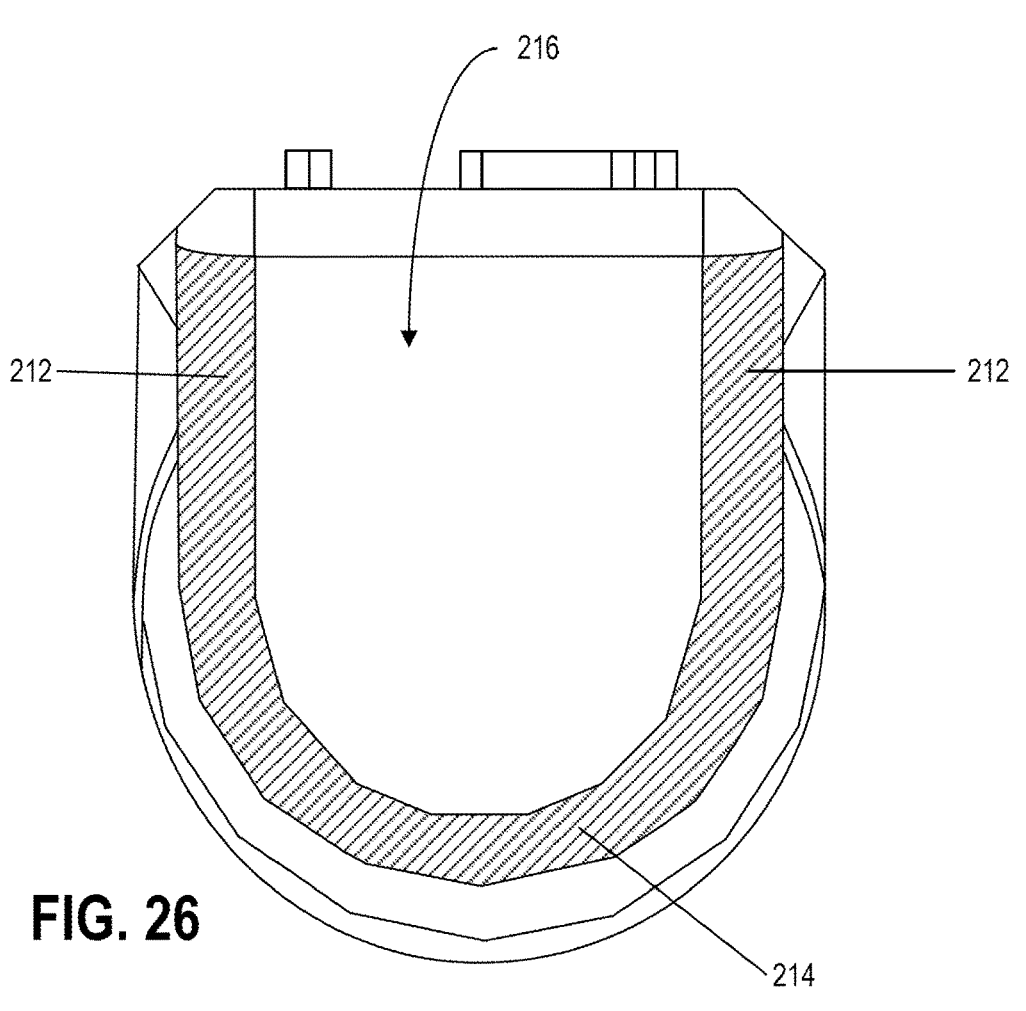
FIG. 26 is a sectional view of the lateral implant removal tool shown in FIG. 22 taken along line 26-26 in FIG. 23.
Figure 27:
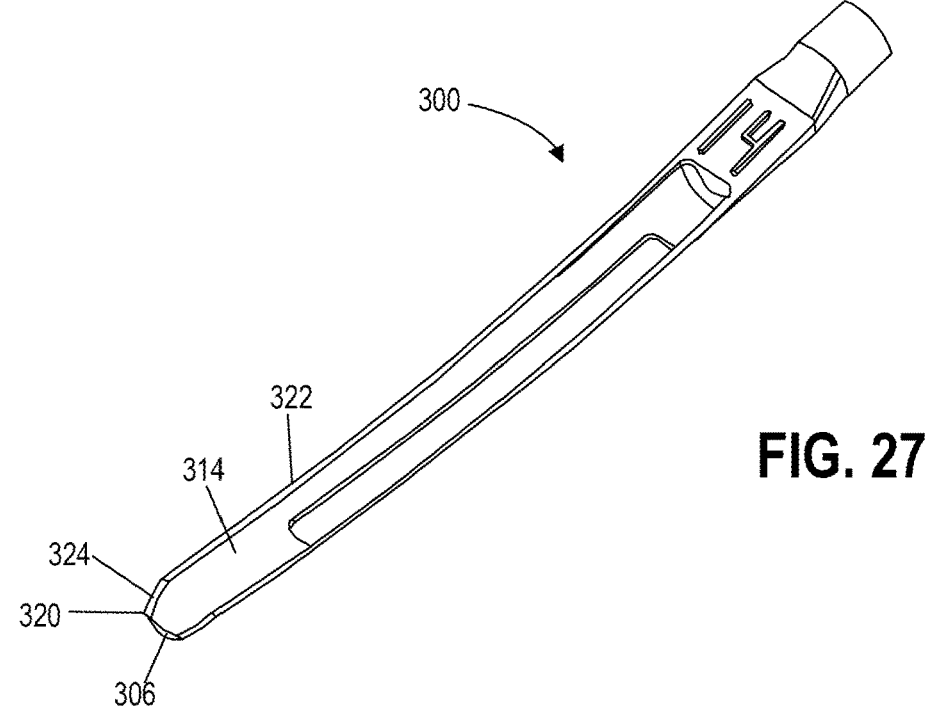
FIG. 27 is a perspective view of a further alternative embodiment of the lateral implant removal tool.
Figure 28:
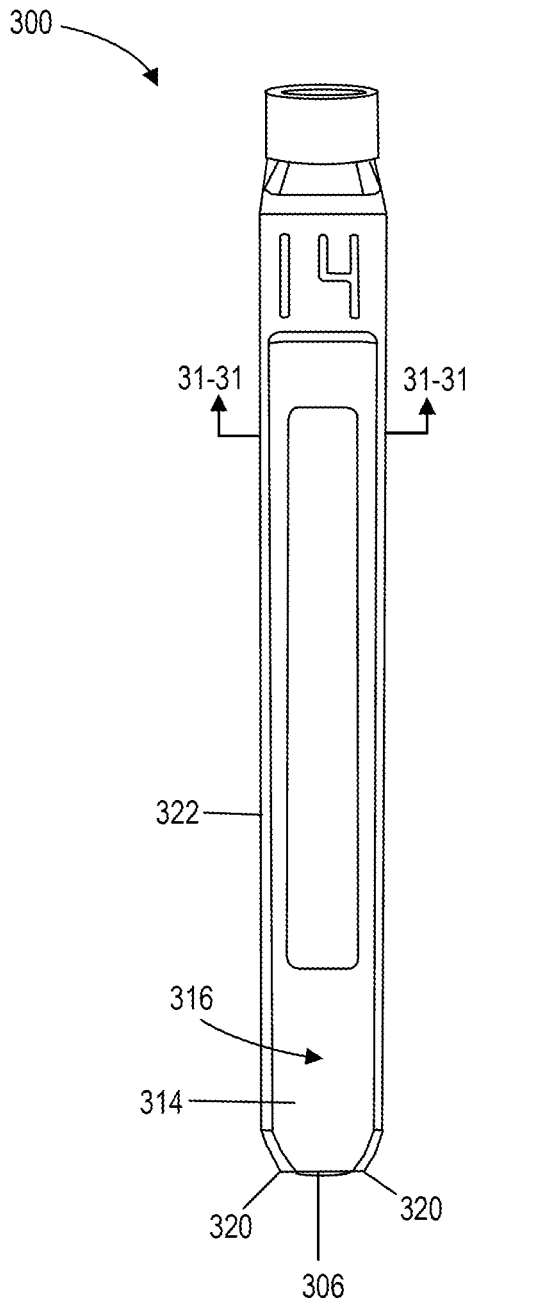
FIG. 28 is a front view of the lateral implant removal tool shown in FIG. 27.
Figure 29:
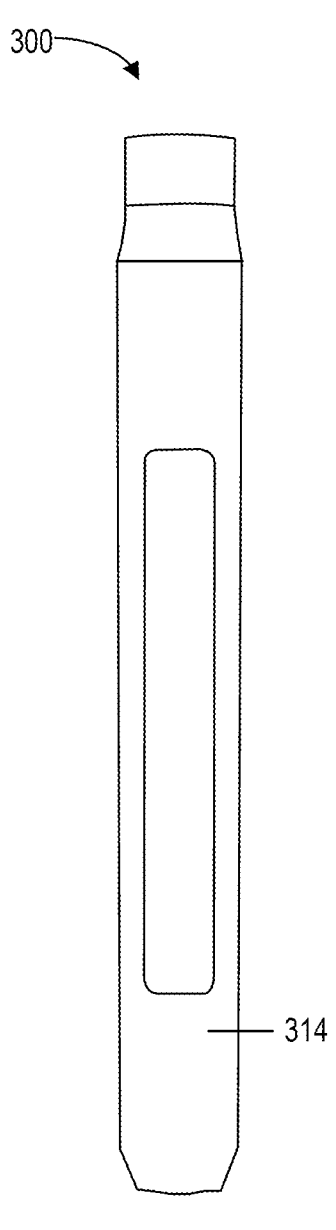
FIG. 29 is a back view of the lateral implant removal tool shown in FIG. 27.
Figures 30, 31:
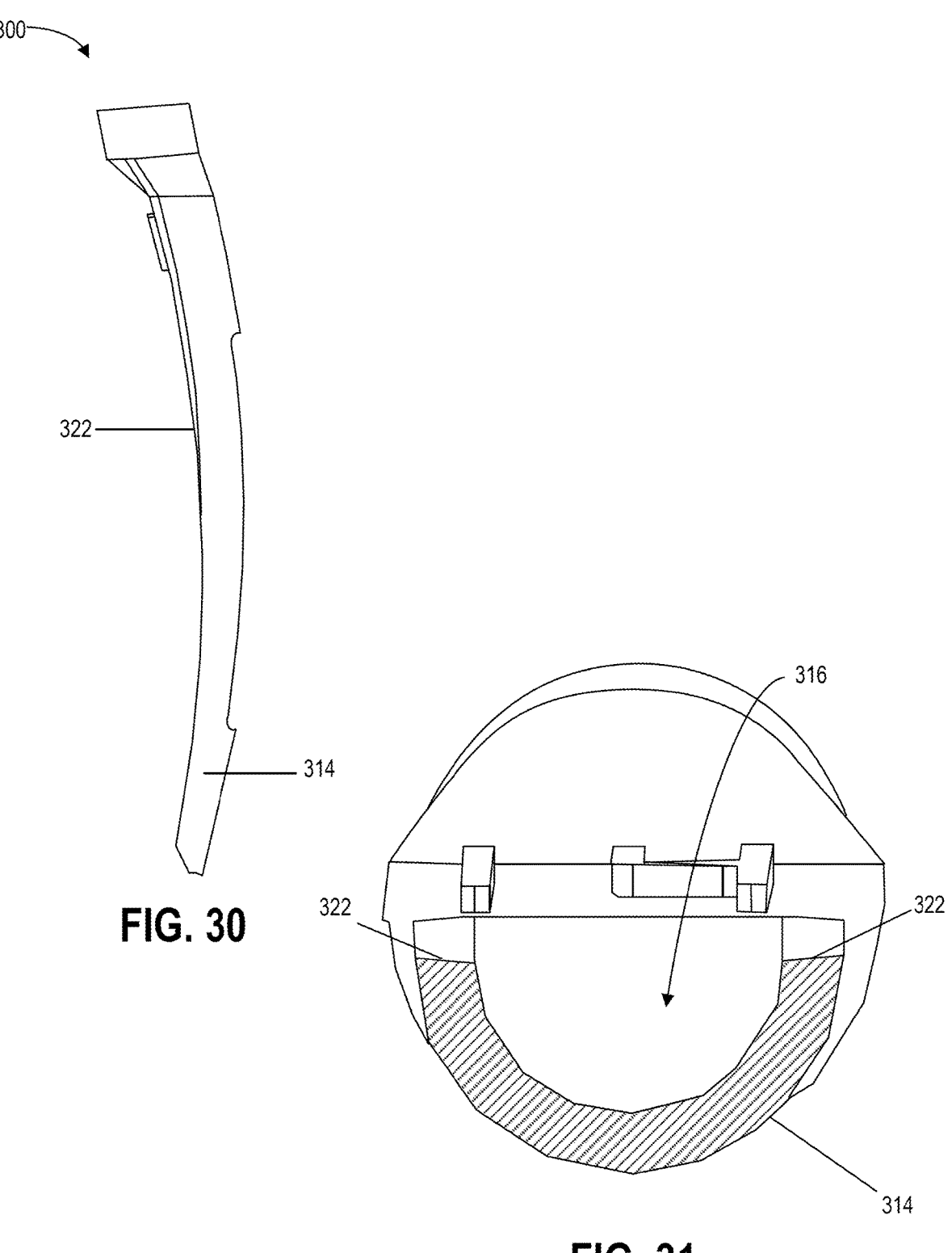
FIG. 30 is a side view of the lateral implant removal tool shown in FIG. 27.
FIG. 31 is a sectional view of the lateral implant removal tool shown in FIG. 27 taken along line 31-31 in FIG. 28.

Indicia 210 may be used for identification. As shown in FIGS. 22 and 24, as a non-limiting example, an indicia "14" is used to indicate that the opening along the arcuate blade is 14 mm wide. Other sizes are possible, as are indicia identifying the tool by another criterion.

Although the shape of femoral implants varies, oftentimes the inside surface of lateral wall 214 has an extent that is curved to match the lateral side contour of a femoral implant. In some embodiments, side edges 222 are sharpened or configured for cutting and are curved or arcuate. Side edges 222 should be understood as the edges on the sides of lateral tool 200 and could be edges of side walls 212 or lateral wall 214. In some embodiments, lateral tool 200 may have side walls 212 having height tapered from proximal end 202 to distal end 204.

Still with reference to lateral tool 200 in FIGS. 22-26, all edges surrounding interior area 216 may be sharpened or configured for cutting to facilitate insertion of lateral tool 200 into a femur. These edges cut along bone and implant interface and otherwise allow for the insertion of lateral tool 200 into a femur. In some aspects, these edges may be configured with teeth or scalloped edges to aid in the cutting of bone.

While, as described above, leading edge 206 may be curved between two pointed ends 220, alternatively, leading edge 206 may instead comprise one or more straight edges between pointed ends 220. Leading edge 206 may include one or more teeth or scalloped edges to facilitate insertion into the femur. Leading edge 206, side edges 222, and the extent of the interior of lateral wall 214 allow lateral tool 200 to be inserted as closely as possible along the interface between a femur and implant. This advantageously allows for the efficient removal of the implant.

In FIG. 23-24, opening 218 is shown as rectangular in shape, having a length along a longitudinal axis of lateral tool 200 that is greater than a width. Corners of opening 218 may include chamfers or may be rounded as illustrated. A proximal opening edge 228, a distal opening edge 230, or side opening edges 232 may include sharpened edges, rounded edges, or blunt edges. Opening 218 is shaped so that certain features of an implant may pass through as lateral tool 200 advances into a femur. More particularly, opening 218 allows the shape of interior area 216 of lateral tool 200 to not completely conform to the shape of the lateral side of the implant so that side edges 222 may cut closely along the implant/bone interface. Therefore, the shape of opening 218 can be customized for an implant to be removed. For example, while opening 218 is shown as being rectangular, it may have another shape such as an ellipse or oval. Lateral tool 200 may also include more than one opening. Opening 218 may be arranged over a smaller portion of lateral tool 200.

As described with reference to previous embodiments, in order to allow a surgeon to gauge how far a lateral tool has been inserted, a window (not shown) or other measuring feature can be formed within one or both of side walls 212, or on lateral wall 214.

In some exemplary embodiments, as shown in FIG. 27-31, lateral tool 300 is similar to lateral tool 200, except that lateral tool 300 has side walls 312 with height that tapers off quickly so that side edges 322 become edges of lateral wall 314, and interior area 316 becomes the area defined by the inside surface of the arcuate lateral wall 314. Bevels 324 may be formed on the side walls 312 or lateral wall 314 and angled to pointed ends 320. In some embodiments, the bevels 324 are sharpened or configured for cutting.

Figure 32:
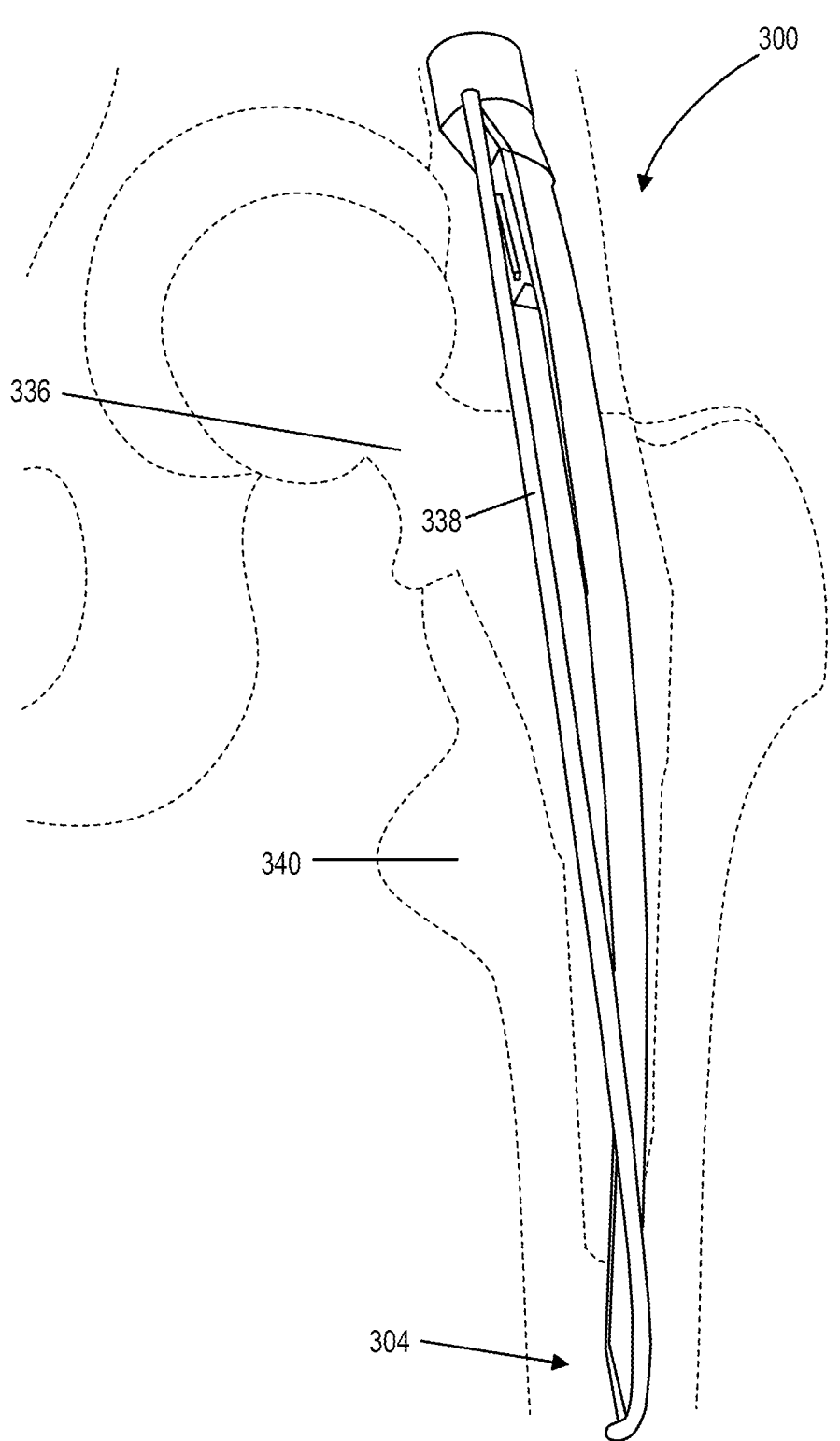
FIG. 32 is an illustration of the lateral implant removal tool shown in FIG. 27 working in combination with a Gigli saw.
Figures 33, 34:
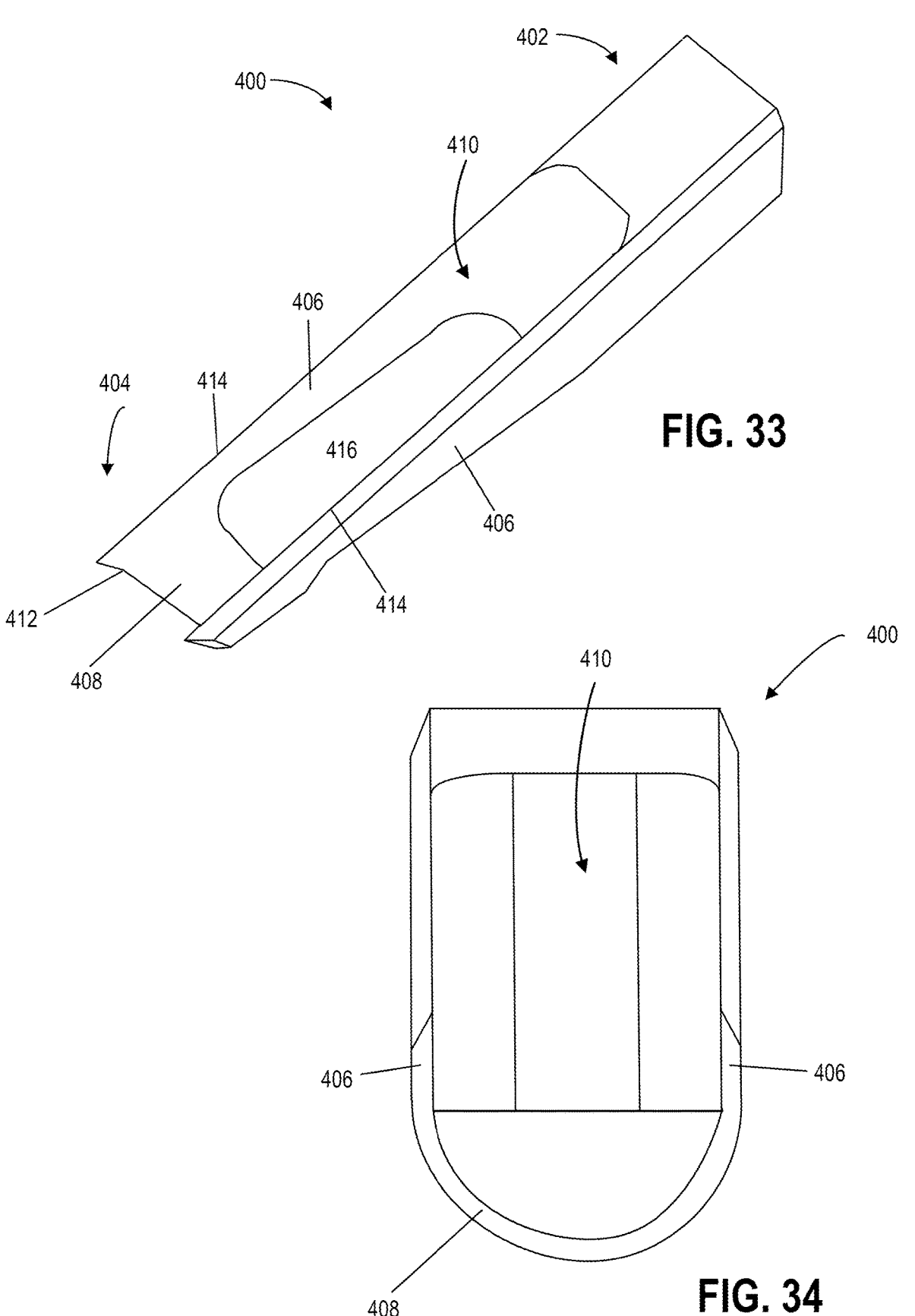
FIG. 33 is a perspective view of yet another alternative embodiment of the lateral implant removal tool.
FIG. 34 is an end view of the lateral implant removal tool shown in FIG. 33.
Figure 35:
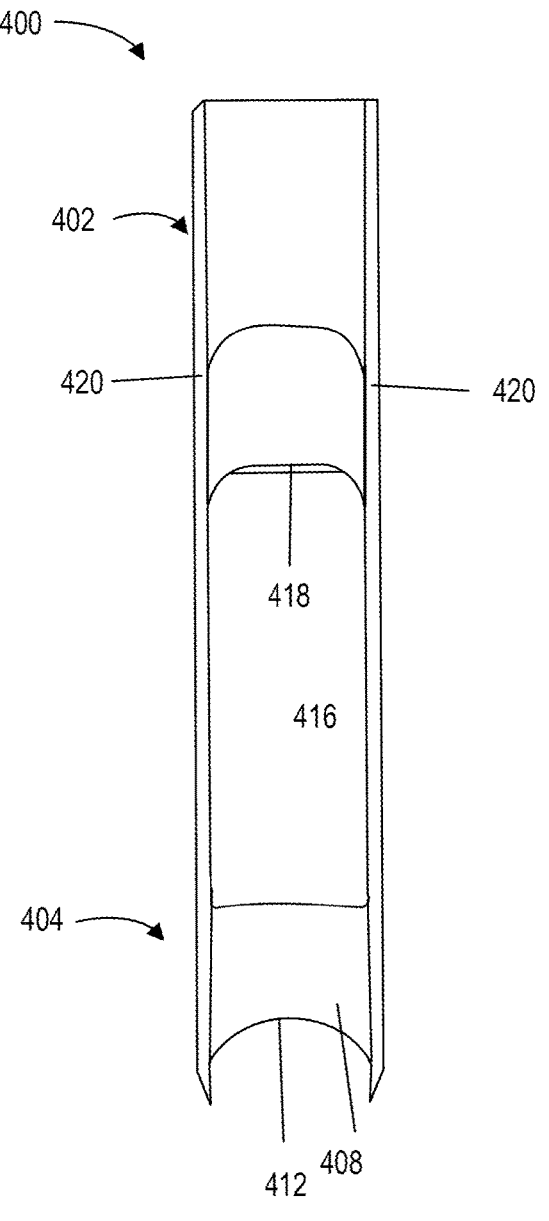
FIG. 35 is a front view of the lateral implant removal tool shown in FIG. 33.
Figure 36:
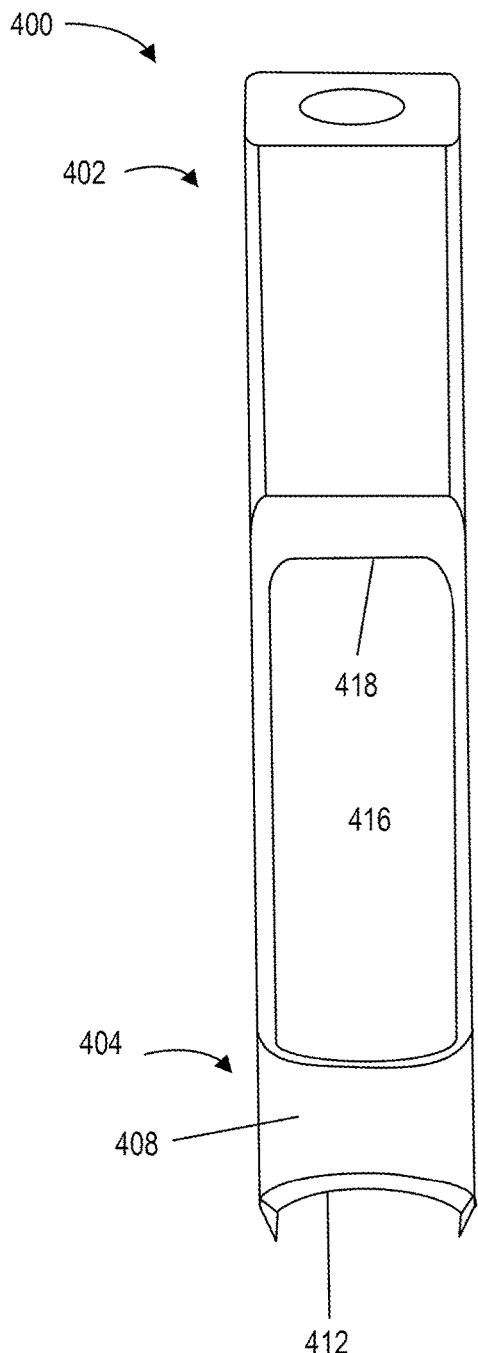
FIG. 36 is a back view of the lateral implant removal tool shown in FIG. 33.
Figure 37:
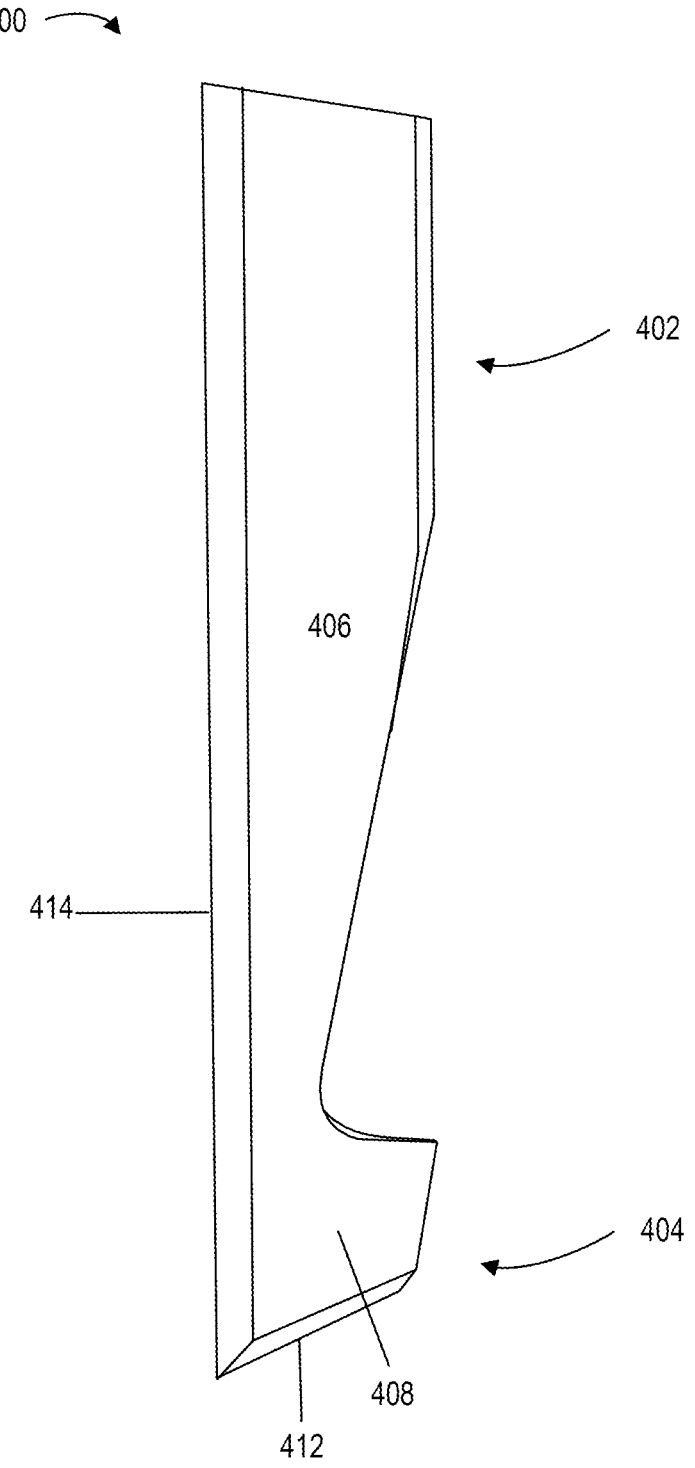
FIG. 37 is a side view of the lateral implant removal tool shown in FIG. 33.

In one embodiment, as depicted in FIG. 32, a distal end 304 of lateral tool 300 can be configured to accommodate a Gigli saw 334, or other instrument, such that once lateral tool 300 is inserted along an implant 336, Gigli saw 334 can be used by a surgeon to cut along the implant 336 to facilitate removal of the implant. Advantageously, saw wire 338 can be crossed around the implant before introduction which can allow Gigli saw 334 to help release the lateral, medial, anterior, and posterior aspects of the implant 336 from the bone 340. Although Gigli saw 334 is shown only in FIG. 32, it can be used with other examples in this disclosure as well.

FIGS. 33-37 depicts yet another alternative embodiment of a lateral tool as a lateral tool 400. Lateral tool 400 has a proximal end 402 and a distal end 404. As shown in a front view of lateral tool 400 in FIG. 34, lateral tool 400 has two parallel side walls 406 and a lateral wall 408 with a curved shape cross section, defining an interior area 410. A leading edge 412 and side edges 414 around interior area 410 may be sharpened or configured for cutting the lateral side, anterior side, and posterior side of an implant together as lateral tool 400 advances into a femur.

Lateral wall 408 of lateral tool 400 may be substantially straight longitudinally, having a longitudinal axis at an angle to side edges 414. An opening 416 may displace a substantial portion of lateral wall 408 as well as sections of adjacent side walls 406, leaving lateral wall 408 present only near distal end 404 of lateral tool 400. The cross sectional shape of lateral wall 408 can be customized to conform the shape of the lateral side of an implant to be removed. Advantageously, a shorter lateral wall 408 may enable lateral tool 400 to conform to implants with a larger variety of lateral curvature. Side edges 414 may be sharpened or configured for cutting along an anterior side and a posterior side of an implant. In this exemplary embodiment, side edges 414 are straight. However, side edges 414 can be curved or arcuate, or have segments at different angles to facilitate cutting the anterior and posterior sides of the implant.

Figure 38:
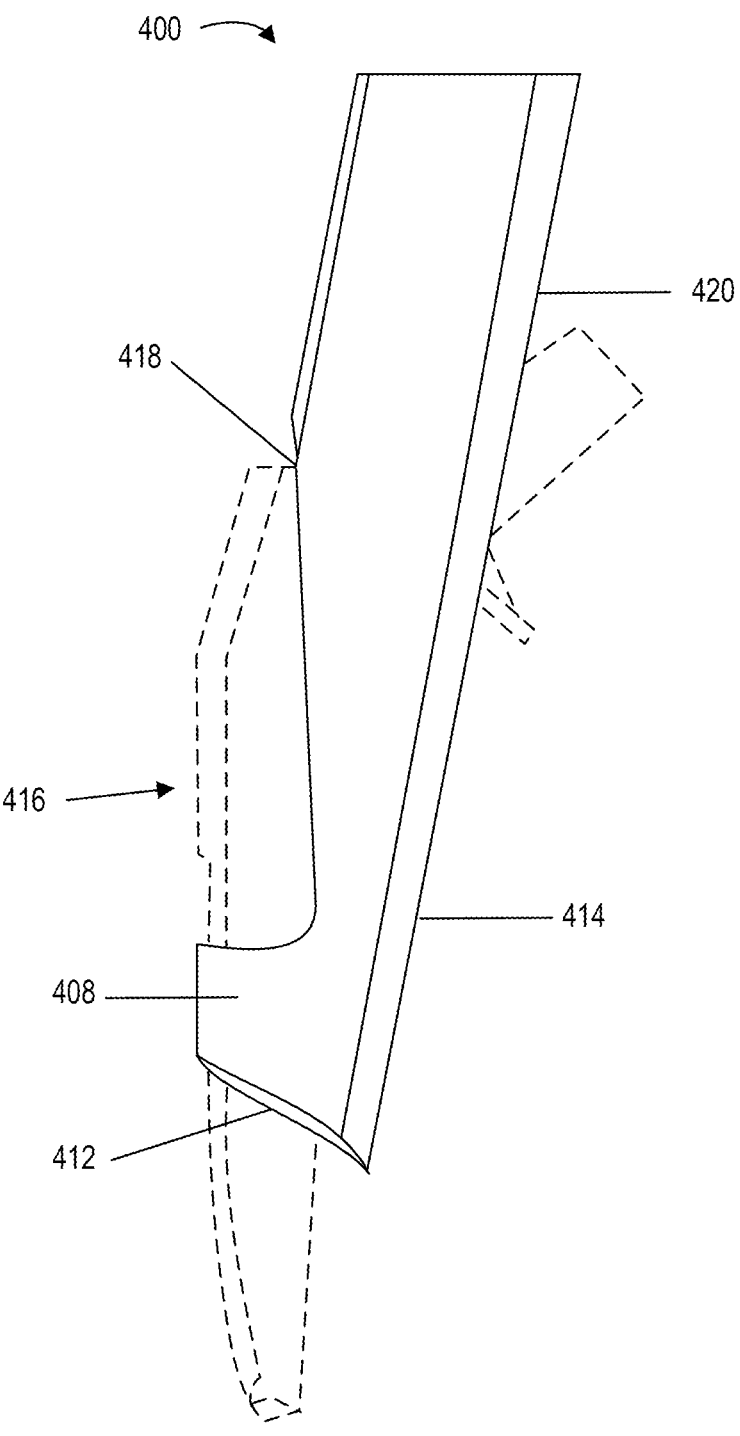
FIG. 38 is an illustration of full insertion of the lateral implant removal tool shown in FIG. 33.
Figure 39:
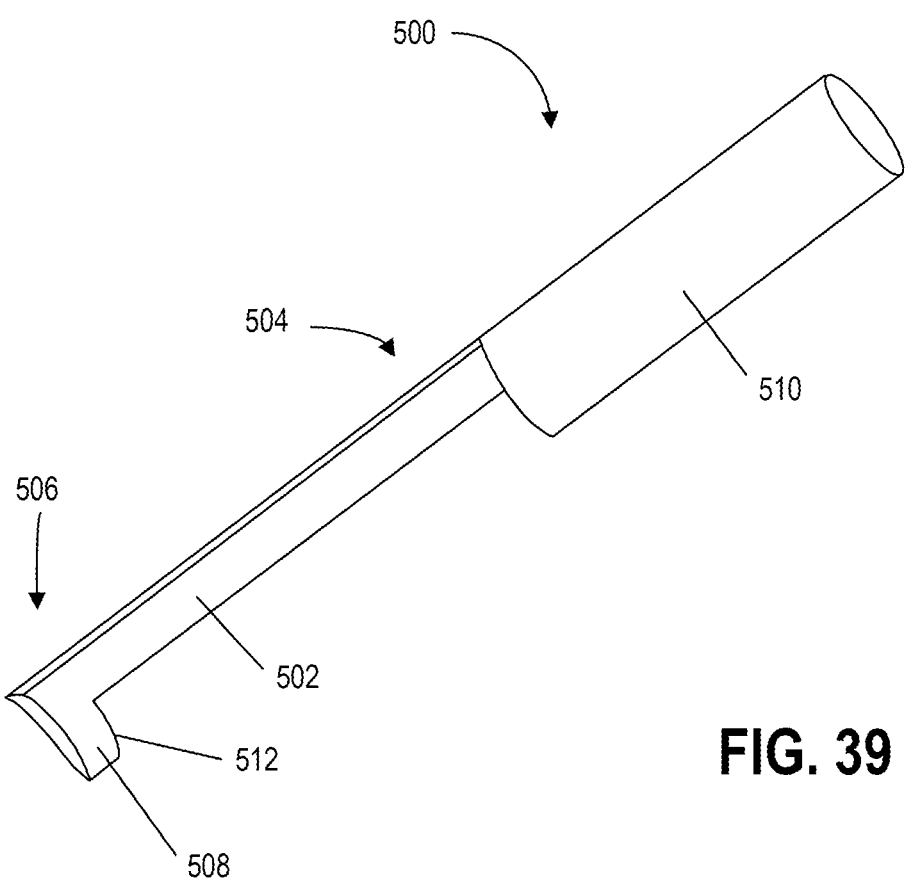
FIG. 39 is a perspective view of an embodiment of a J-shaped tool.
Figure 40:
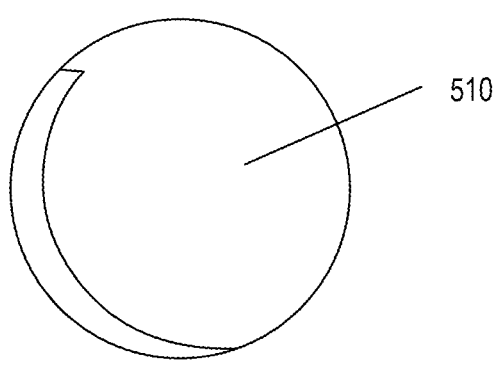
FIG. 40 is an end view of the J-shaped tool shown in FIG. 39.
Figures 43, 44:
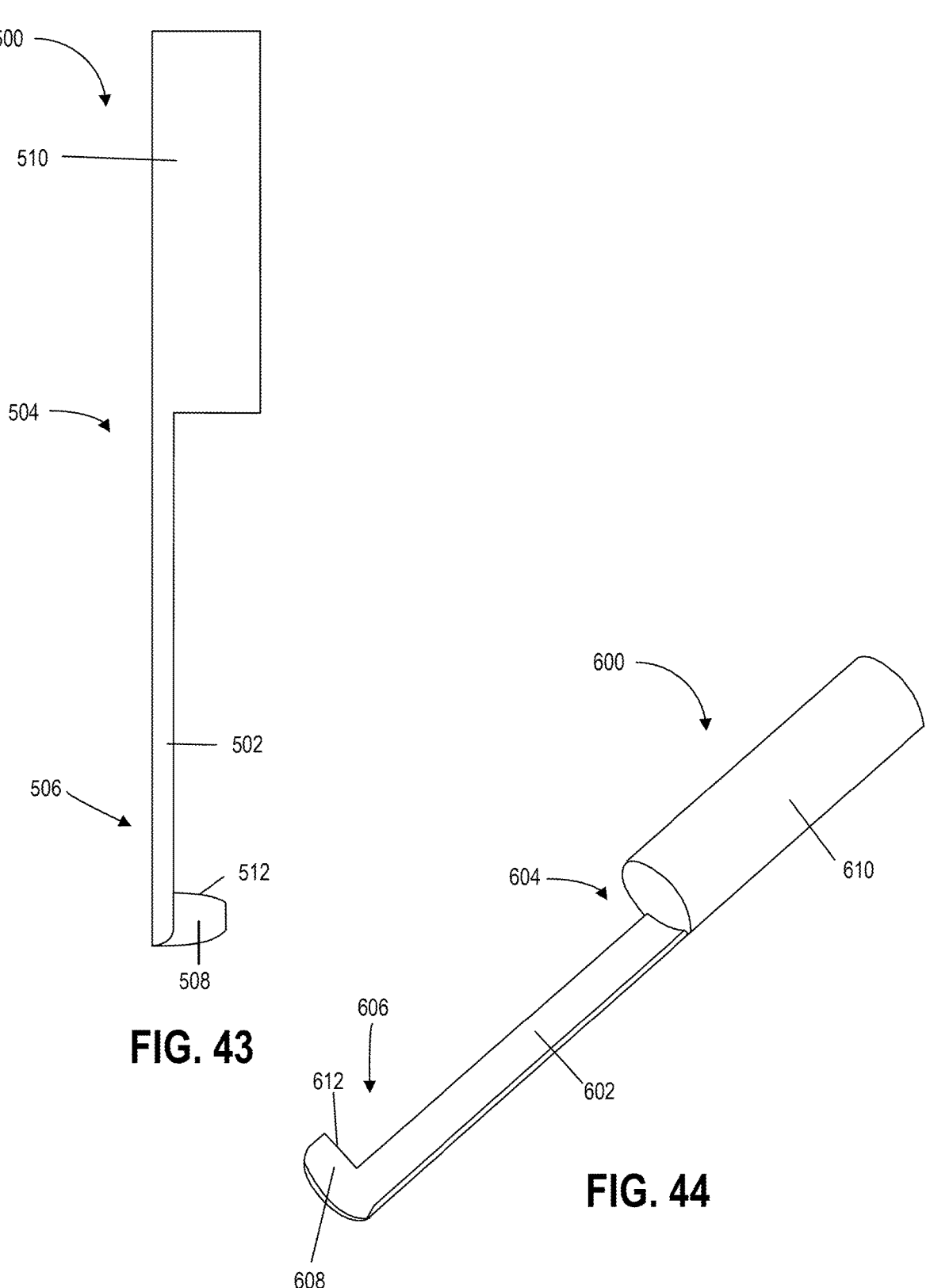
FIG. 43 is a side view of the J-shaped tool shown in FIG. 39.
FIG. 44 is a perspective view of an embodiment of an L-shaped tool.
Figure 45:
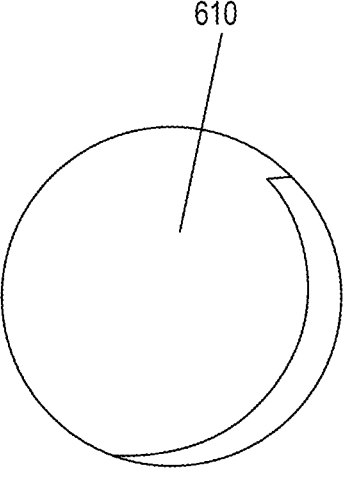
FIG. 45 is an end view of the L-shaped tool shown in FIG. 44.
Figure 46:
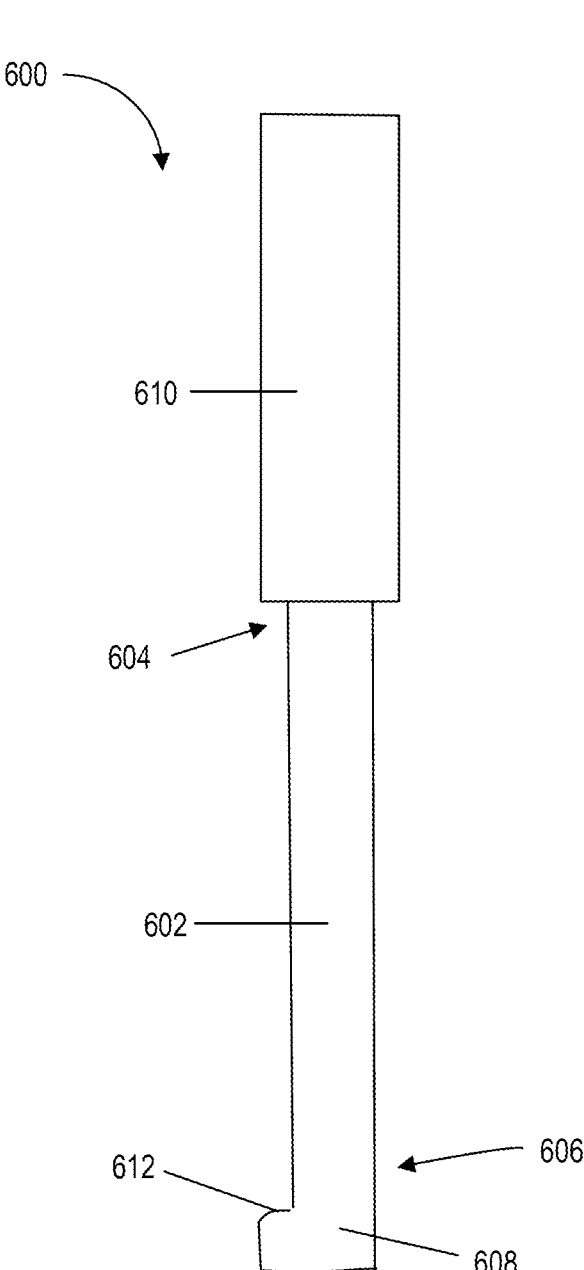
FIG. 46 is a front view of the L-shaped tool shown in FIG. 44.

Opening 416 may have edges sharpened or configured for cutting and is large enough to allow features of implant to pass through as lateral tool 400 advances into a femur, as illustrated in FIG. 38. In this exemplary embodiment, a portion of the implant does not conform to the shape of lateral tool 400 interior area 410 and extends out through opening 416. Opening 416 may be shorter than side edges 414. A proximal edge 418 of opening 416 is on the distal side of proximal ends 420 of side edges 414. However, proximal edge 418 of opening 416 can be proximate to proximal end of side edge 414.

Proximal end 402 of lateral tool 400 may have a proximal connector 422. In some embodiments, proximal connector 422 may include a threaded aperture, a friction-fit connection, a twist lock, or other connector that allows for releasable connection to an impact hammer. In other aspects, proximal connector 422 may allow for releasable connection to a handle or other instruments, such as a vibration generating device. Proximal connector 422 may also include a quick release mechanism or a more permanent securement mechanism. As depicted in FIGS. 33-37, proximal connector 422 may be in-line or parallel to the axis of straight lateral wall 408 with an offset. Advantageously, a surgeon or an operator of lateral tool 400 may apply force through an attachment to proximal connector 422 in an optimal orientation to facilitate leading edge 412 advancing into a femur. However, proximal connector 422 may be customized to be at an angle to the axis of straight lateral wall 408 to optimize for a specific type of implant to be removed.

Undercut Tools

In some embodiments, a J-shaped tool 500 depicted in FIGS. 39-43 or an L-shaped tool 600 depicted in FIGS. 44-48 can be used when an implant has a flange near its stem. J-shaped tool 500 and L-shaped tool 600 are each essentially formed from a portion of a cylindrical shell. J-shaped tool 500 has a straight blade 502 with a proximal end 504 and a distal end 506 and a hook 508 connected to distal end 506 of straight blade 502. Proximal end 506 is connected to a cylindrical tool base 510. Hook 508 includes a proximal edge 512 sharpened or configured for cutting. L-shaped tool 600 has a straight blade 602 with a proximal end 604 and distal end 606 of straight blade 602. Proximal end 606 is connected to a cylindrical tool base 610. Tool base 510 or 610 can be any other shape and can include features to facilitate handling. Hook 608 includes a proximal edge 512 sharpened or configured for cutting. Hook 508 or 608 respectively extends from distal end 506 or 606 circumferentially, following the same cylindrical curvature. All edges of straight blade 502 or 602 and hook 508 or 608 may be sharpened or configured for cutting.

Figure 49:
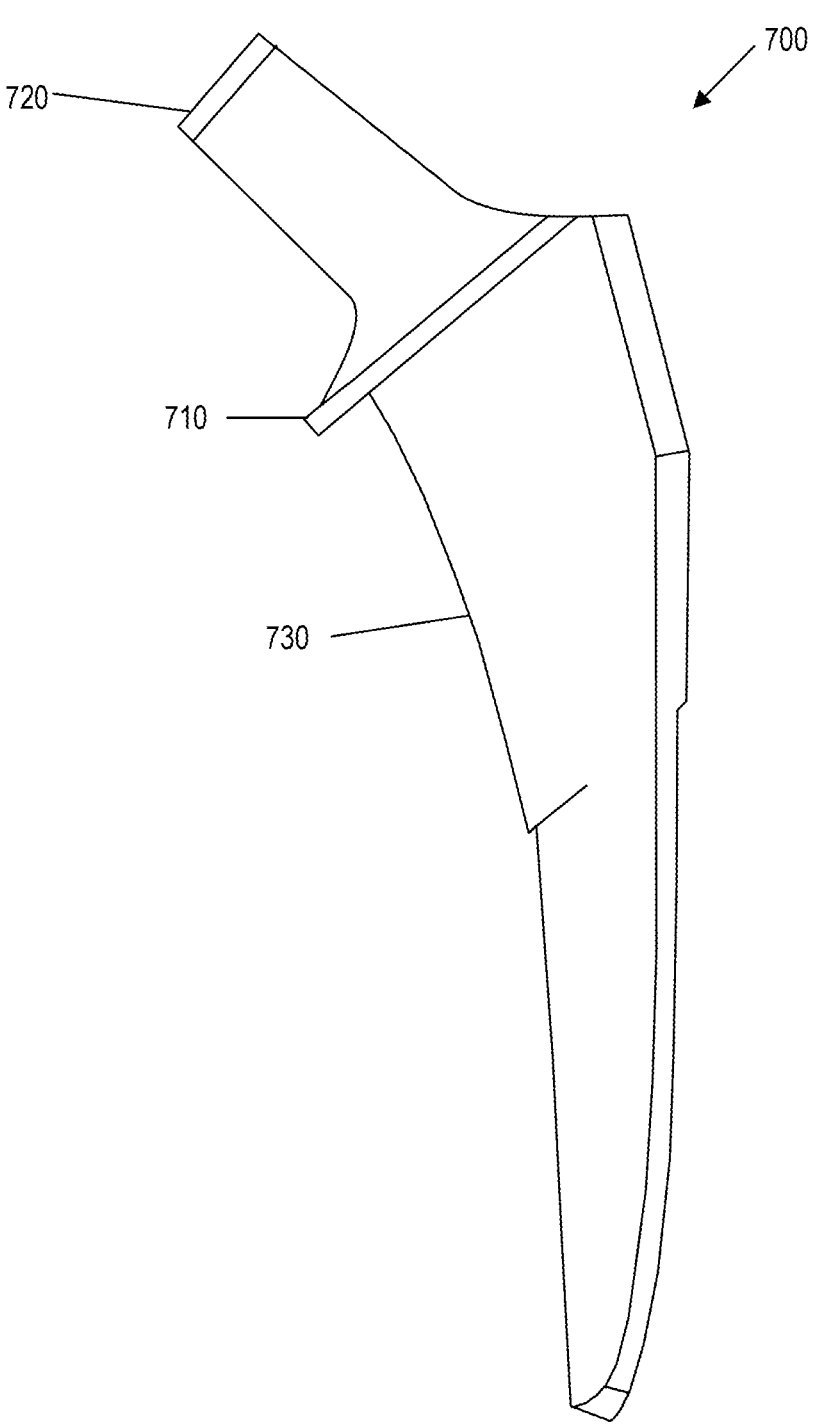
FIG. 49 is an illustration of a femoral implant with a flange.

FIG. 49 illustrates a femoral implant 700. In some embodiments as illustrated in FIG. 49, an implant 700 may include a flange 710 near its stem 720, leaving a medial side 730 being an undercut. Implant 700 may be removed when J-shaped tool 500 or L-shaped tool 600 is advanced into a femur before or after using other lateral and/or medial tools, rotated to have hook 508 or 608 below flange 710, then pulled along medial side 730 while cutting along the implant/bone interface under flange 710 of implant 700, using proximal edge 512 or 612 of hook 508 or 608. This allows J-shaped tool 500 or L-shaped tool 600 to cut around the undercut of an implant.

Figure 50:
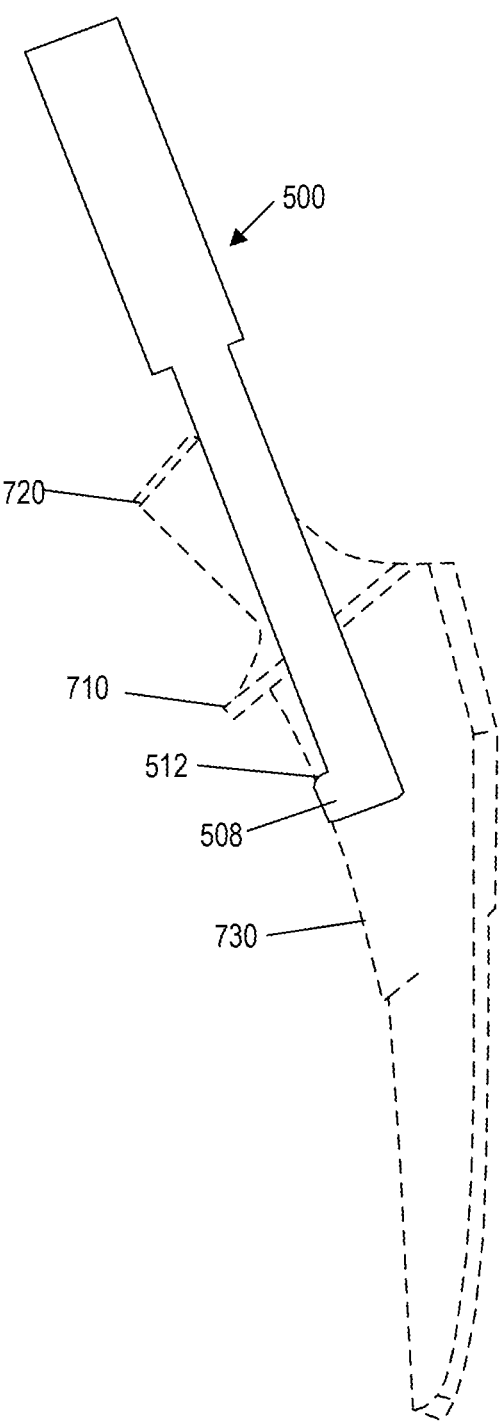
FIG. 50 is an illustration of the J-shaped tool shown in FIG. 39 cutting under the flange of the femoral implant illustrated in FIG. 49.

FIG. 50 illustrates J-shaped tool 500 cutting along medial side 730 of implant 700. One skilled in the art will now appreciate how L-shaped tool 600 is utilized to perform similar tasks. One skilled in the art would also appreciate how J-shaped tool 500 and L-shaped tool 600 can cut around flanges at a different location of an implant.

The disclosed tools and tool set have several advantages. For example, the tools in the tool set are shaped to conform to the interface between bone and a prosthetic, such as a femoral implant. The tools may also include an opening to accommodate a neck or other features of the prosthetic to pass through, so that the shape of an interior area of the tools does not have to fully conform to the shape of the implant to allow cutting along the implant/bone interface. Edges on both sides and around the opening may be sharpened or configured for cutting, so the tool may cut along anterior and posterior sides of the implant while at the same time cutting along the lateral or medial aspect. All of this allows inserting tools along an edge of a prosthetic that is immediately adjacent to a stem or other feature of a prosthetic, enabling efficient removal of the prosthetic.

An advantage of the tools of the present disclosure is that they allow prosthetics to be removed efficiently and in a minimal amount of time.

A further advantage of the tools is that they allow prosthetics to be removed while minimizing the loss of existing bone.

Yet a further advantage of the tools is that the efficient removal of prosthetics greatly decreases recovery time.

Another advantage is that the efficient removal of prosthetics reduces both the need for anesthesia and operating room costs in general.

In one embodiment, a tool provides a groove or recess for accommodating an additional cutting element such as a Gigli saw to further facilitate removal of an implant, which allows for the efficient removal of the prosthetic.

Various embodiments of the disclosure may have none, some, or all of these advantages. Other technical advantages of the present disclosure will be readily apparent to one skilled in the art.

Although this disclosure has been described in terms of certain embodiments and generally associated methods, alterations and permutations of these embodiments and methods will be apparent to those skilled in the art. Accordingly, the above description of example embodiments does not define or constrain this disclosure. Other changes, substitutions, and alterations are also possible without departing from the spirit and scope of this disclosure.

What is claimed is:

1. A tool for removal of a femoral implant, comprising:
a proximal end;
a proximal connector near the proximal end;
a distal end having a leading edge;
a lateral wall that is arcuate, allowing the distal end to penetrate into a femur substantially closely along a lateral side of the femoral implant, wherein the lateral wall includes at least one opening allowing features of an implant to be removed to pass through; and
side edges extending from the proximal end to the distal end and configured for cutting.

2. The tool of claim 1, wherein the side edges are curved.

3. The tool of claim 1, wherein there is only one opening in the lateral wall.

4. The tool of claim 3, wherein the opening is rectangular in shape and has a length along a longitudinal axis of the tool, the length of the opening being greater than a width of the opening.

5. The tool of claim 3, wherein a proximal edge of the opening is on the distal side of a proximal end of the side edge.

6. The tool of claim 1, wherein the at least one opening has sharpened edges.

7. The tool of claim 1, wherein the leading edge is sharpened.

8. The tool of claim 1, wherein the leading edge has two pointed ends and bevels on a proximal side of the pointed ends, wherein the bevels are sharpened.

9. The tool of claim 8, wherein the leading edge between the two pointed ends is curved.

10. The tool of claim 8, wherein the leading edge between the two pointed ends is straight.

11. The tool of claim 1, wherein the proximal connector is configured for connection to a handle parallel to a cutting plane of the leading edge.

12. The tool of claim 1, wherein the lateral wall has an inside surface profile matching a profile of a lateral side of a femoral implant lateral side.

13. The tool of claim 1, wherein the lateral wall is straight longitudinally.

14. The tool of claim 1, wherein the tool has one or more recesses to accommodate an additional cutting element to further facilitate removal of an implant.

15. The tool of claim 1, wherein the side edges are tapered in height from the proximal end towards the distal end of the tool.

16. The tool of claim 1, wherein at least one indicator is formed between the two side edges to allow gauging how far the tool has been inserted into a femur.

17. The tool of claim 16, wherein the indicator is a window.

18. A tool kit for removal of a femoral implant, comprising:
at least one lateral tool; and
at least one of
at least one medial tool;
a J-shaped tool; or
an L-shaped tool;
wherein the at least one lateral tool comprises:
a lateral tool proximal end;
a lateral tool proximal connector near the lateral tool proximal end;
a lateral tool distal end having a lateral tool leading edge;
a lateral tool lateral wall that is arcuate, allowing the lateral tool distal end to penetrate into a femur substantially closely along a lateral side of the femoral implant; and
lateral tool side edges extending from the lateral tool proximal end to the lateral tool distal end configured for cutting;
wherein the at least one medial tool comprises:
a medial tool proximal end;
a medial tool proximal connector near the medial tool proximal end;
a medial tool distal end having a medial tool leading edge;
a medial tool lateral wall that is arcuate;
side edges extending from the proximal end to the distal end configured for cutting; and
at least one opening located in the medial tool lateral wall allowing a femoral implant to partially pass through as the medial tool advancing into a femur;
wherein the J-shaped and the L-shaped tool each comprises:
a side tool proximal end;
a side tool proximal connector near the side tool proximal end;
a side tool distal end having a side tool leading edge; and
a hook connected to the side tool distal end, wherein all edges of the hook are configured for cutting.

19. A tool for removal of a femoral implant, comprising:
a proximal end;
a proximal connector near the proximal end;
a distal end having a leading edge;
a lateral wall that is arcuate, allowing the distal end to penetrate into a femur substantially closely along a lateral side of the femoral implant; and
side edges extending from the proximal end to the distal end and configured for cutting,
wherein the tool has one or more recesses to accommodate an additional cutting element to further facilitate removal of an implant.

20. A tool for removal of a femoral implant, comprising:
a proximal end;
a proximal connector near the proximal end;
a distal end having a leading edge;
a lateral wall that is arcuate, allowing the distal end to penetrate into a femur substantially closely along a lateral side of the femoral implant; and
side edges extending from the proximal end to the distal end and configured for cutting,
wherein at least one indicator is formed between the two side edges to allow gauging how far the tool has been inserted into a femur.

* * * * *